(12) United States Patent  
Martakos et al.

(10) Patent No.: US 8,574,627 B2
(45) Date of Patent: Nov. 5, 2013

(54) COATED SURGICAL MESH

(75) Inventors: Paul Martakos, Pelham, NH (US);
Steve A. Herweck, Nashua, NH (US);
Jocelyn Prowse, Waltham, MA (US);
Anthony Richard Horton, Manchester, NH (US); Keith M. Faucher, Nashua, NH (US); Joseph Ferraro, Londonderry, NH (US)

(73) Assignee: Atrium Medical Corporation, Hudson, NH (US)

( * ) Notice: Subject to any disclaimer, the term of this patent is extended or adjusted under 35 U.S.C. 154(b) by 1026 days.

(21) Appl. No.: 11/978,840

(22) Filed: Oct. 30, 2007

(65) Prior Publication Data

US 2008/0118550 A1    May 22, 2008

Related U.S. Application Data

(60) Provisional application No. 60/856,983, filed on Nov. 6, 2006.

(51) Int. Cl.
*A61K 9/00* (2006.01)
*A61F 2/00* (2006.01)

(52) U.S. Cl.
USPC .................... 424/484; 424/523; 514/458

(58) Field of Classification Search
None
See application file for complete search history.

(56) References Cited

U.S. PATENT DOCUMENTS

| 2,368,306 A | 1/1945 | Kiefer et al. |
|---|---|---|
| 2,986,540 A | 5/1961 | Posnansky |
| 3,464,413 A | 9/1969 | Goldfarb et al. |
| 3,556,294 A | 1/1971 | Walck et al. |
| 3,567,820 A | 3/1971 | Sperti |
| 3,803,109 A | 4/1974 | Nemoto et al. |
| 3,967,728 A | 7/1976 | Gordon et al. |
| 4,308,120 A | 12/1981 | Pennewiss et al. |
| 4,323,547 A | 4/1982 | Knust et al. |
| 4,557,925 A | 12/1985 | Lindahl et al. |
| 4,664,114 A | 5/1987 | Ghodstain |
| 4,813,210 A | 3/1989 | Masuda et al. |
| 4,814,329 A | 3/1989 | Harsanyi et al. |

(Continued)

FOREIGN PATENT DOCUMENTS

| EP | 0 471 566 | 2/1992 |
|---|---|---|
| EP | 0610731 | 8/1994 |

(Continued)

OTHER PUBLICATIONS

"Surface coating." Encyclopædia Britannica. Encyclopædia Britannica Online. Encyclopædia Britannica, 2011. Web. Jun. 17, 2011. <http://www.britannica.com/EBchecked/topic/575029/surface-coating>.*

(Continued)

*Primary Examiner* — Allison Ford
(74) *Attorney, Agent, or Firm* — Morse, Barnes-Brown & Pendleton, P.C.; Sean D. Detweiler, Esq.

(57) ABSTRACT

A surgical mesh is formed of a biocompatible mesh structure with a coating that provides anti-inflammatory, non-inflammatory, and anti-adhesion functionality for a implantation in a patient. The coating is generally formed of a fish oil, can include vitamin E, and may be at least partially cured. In addition, the coating can include a therapeutic agent component, such as a drug or other therapeutic agent.

25 Claims, 13 Drawing Sheets

(56) References Cited

U.S. PATENT DOCUMENTS

| | | |
|---|---|---|
| 4,847,301 A | 7/1989 | Murray |
| 4,880,455 A | 11/1989 | Blank |
| 4,883,667 A | 11/1989 | Eckenhoff |
| 4,886,787 A | 12/1989 | De Belder et al. |
| 4,894,231 A | 1/1990 | Moreau et al. |
| 4,895,724 A | 1/1990 | Cardinal et al. |
| 4,911,707 A | 3/1990 | Heiber et al. |
| 4,941,308 A | 7/1990 | Grabenkort et al. |
| 4,952,419 A | 8/1990 | De Leon |
| 4,968,302 A | 11/1990 | Schluter et al. |
| 5,017,229 A | 5/1991 | Burns et al. |
| 5,132,115 A | 7/1992 | Wolter et al. |
| 5,147,374 A | 9/1992 | Fernandez |
| 5,151,272 A | 9/1992 | Engstrom et al. |
| 5,171,148 A | 12/1992 | Wasserman et al. |
| 5,176,956 A | 1/1993 | Jevne et al. |
| 5,179,174 A | 1/1993 | Elton |
| 5,254,105 A | 10/1993 | Haaga |
| 5,356,432 A | 10/1994 | Rutkow et al. |
| 5,368,602 A | 11/1994 | De La Torre |
| 5,371,109 A | 12/1994 | Engstrom et al. |
| 5,380,328 A | 1/1995 | Morgan |
| 5,387,658 A | 2/1995 | Schroder et al. |
| 5,403,283 A | 4/1995 | Luther |
| 5,447,940 A | 9/1995 | Harvey et al. |
| 5,464,650 A | 11/1995 | Berg et al. |
| 5,480,653 A | 1/1996 | Aguadisch et al. |
| 5,509,899 A | 4/1996 | Fan et al. |
| 5,579,149 A | 11/1996 | Moret et al. |
| 5,580,923 A | 12/1996 | Yeung et al. |
| 5,591,230 A | 1/1997 | Horn et al. |
| 5,593,441 A | 1/1997 | Lichtenstein et al. |
| 5,612,074 A | 3/1997 | Leach |
| 5,614,284 A | 3/1997 | Kranzler et al. |
| 5,627,077 A | 5/1997 | Dyllick-Brenzinger et al. |
| 5,637,113 A | 6/1997 | Tartaglia et al. |
| 5,665,115 A | 9/1997 | Cragg |
| 5,695,525 A | 12/1997 | Mulhauser et al. |
| 5,700,286 A | 12/1997 | Tartaglia et al. |
| 5,736,152 A | 4/1998 | Dunn |
| 5,753,259 A | 5/1998 | Engstrom et al. |
| 5,760,081 A | 6/1998 | Leaf et al. |
| 5,766,246 A | 6/1998 | Mulhauser et al. |
| 5,766,710 A | 6/1998 | Turnlund et al. |
| 5,789,465 A | 8/1998 | Harvey et al. |
| 5,817,343 A | 10/1998 | Burke |
| 5,824,082 A | 10/1998 | Brown |
| 5,837,313 A | 11/1998 | Ding et al. |
| 5,843,919 A | 12/1998 | Burger |
| 5,874,470 A | 2/1999 | Nehne et al. |
| 5,879,359 A | 3/1999 | Dorigatti et al. |
| 5,898,040 A | 4/1999 | Shalaby et al. |
| 5,906,831 A | 5/1999 | Larsson et al. |
| 5,931,165 A | 8/1999 | Reich et al. |
| 5,955,502 A | 9/1999 | Hansen et al. |
| 5,986,043 A | 11/1999 | Hubbell et al. |
| 6,005,004 A | 12/1999 | Katz et al. |
| 6,010,766 A | 1/2000 | Braun et al. |
| 6,010,776 A | 1/2000 | Exsted et al. |
| 6,015,844 A | 1/2000 | Harvey et al. |
| 6,028,164 A | 2/2000 | Loomis |
| 6,040,330 A | 3/2000 | Hausheer et al. |
| 6,056,970 A | 5/2000 | Greenawalt et al. |
| 6,077,698 A | 6/2000 | Swan et al. |
| 6,083,950 A | 7/2000 | Anand et al. |
| 6,090,809 A | 7/2000 | Anand et al. |
| 6,093,792 A | 7/2000 | Gross et al. |
| 6,117,911 A | 9/2000 | Grainger et al. |
| 6,120,789 A | 9/2000 | Dunn |
| 6,132,765 A | 10/2000 | DiCosmo et al. |
| 6,146,358 A | 11/2000 | Rowe |
| 6,152,944 A | 11/2000 | Holman et al. |
| 6,176,863 B1 | 1/2001 | Kugel et al. |
| 6,193,746 B1 | 2/2001 | Strecker |
| 6,197,357 B1 | 3/2001 | Lawton et al. |
| 6,203,551 B1 | 3/2001 | Wu |
| 6,206,916 B1 | 3/2001 | Furst |
| 6,211,315 B1 | 4/2001 | Larock et al. |
| 6,228,383 B1 | 5/2001 | Hansen et al. |
| 6,229,032 B1 | 5/2001 | Jacobs et al. |
| 6,245,811 B1 | 6/2001 | Harrobin et al. |
| 6,254,634 B1 | 7/2001 | Anderson et al. |
| 6,262,109 B1 | 7/2001 | Clark et al. |
| 6,273,913 B1 | 8/2001 | Wright et al. |
| 6,284,268 B1 | 9/2001 | Mishra et al. |
| 6,299,604 B1 | 10/2001 | Ragheb et al. |
| 6,326,360 B1 | 12/2001 | Kanazawa et al. |
| 6,331,568 B1 | 12/2001 | Horrobin |
| 6,342,254 B1 | 1/2002 | Soudant et al. |
| 6,346,110 B2 | 2/2002 | Wu |
| 6,358,556 B1 | 3/2002 | Ding et al. |
| 6,364,893 B1 | 4/2002 | Sahatjian et al. |
| 6,368,658 B1 | 4/2002 | Schwarz et al. |
| 6,369,039 B1 | 4/2002 | Palasis et al. |
| 6,387,379 B1 | 5/2002 | Goldberg et al. |
| 6,410,587 B1 | 6/2002 | Grainger et al. |
| 6,444,318 B1 | 9/2002 | Guire et al. |
| 6,451,373 B1 | 9/2002 | Hossainy et al. |
| 6,465,525 B1 | 10/2002 | Guire et al. |
| 6,471,980 B2 | 10/2002 | Sirhan et al. |
| 6,479,683 B1 | 11/2002 | Abney et al. |
| 6,491,938 B2 | 12/2002 | Kunz |
| 6,500,453 B2 | 12/2002 | Brey et al. |
| 6,503,556 B2 | 1/2003 | Harish et al. |
| 6,525,145 B2 | 2/2003 | Gevaert et al. |
| 6,527,801 B1 | 3/2003 | Dutta |
| 6,534,693 B2 | 3/2003 | Fischell et al. |
| 6,548,081 B2 | 4/2003 | Sadozai et al. |
| 6,565,659 B1 | 5/2003 | Pacetti et al. |
| 6,569,441 B2 | 5/2003 | Kunz et al. |
| 6,599,323 B2 | 7/2003 | Melican et al. |
| 6,610,035 B2 | 8/2003 | Yang et al. |
| 6,610,068 B1 | 8/2003 | Yang et al. |
| 6,630,151 B1 | 10/2003 | Tarletsky et al. |
| 6,630,167 B2 | 10/2003 | Zhang |
| 6,632,822 B1 | 10/2003 | Rickards et al. |
| 6,641,611 B2 | 11/2003 | Jayaraman |
| 6,645,547 B1 | 11/2003 | Shekalim |
| 6,663,880 B1 | 12/2003 | Roorda et al. |
| 6,669,735 B1 | 12/2003 | Pelissier |
| 6,670,355 B2 | 12/2003 | Azrolan et al. |
| 6,677,342 B2 | 1/2004 | Wolff et al. |
| 6,677,386 B1 | 1/2004 | Giezen et al. |
| 6,685,956 B2 | 2/2004 | Chu et al. |
| 6,730,064 B2 | 5/2004 | Ragheb et al. |
| 6,753,071 B1 | 6/2004 | Pacetti |
| 6,761,903 B2 | 7/2004 | Chen et al. |
| 6,764,509 B2 | 7/2004 | Chinn et al. |
| 6,776,796 B2 | 8/2004 | Falotico et al. |
| 6,794,485 B2 | 9/2004 | Shalaby et al. |
| 6,833,004 B2 | 12/2004 | Ishii et al. |
| 6,852,330 B2 | 2/2005 | Bowman et al. |
| 6,875,230 B1 | 4/2005 | Morita et al. |
| 6,884,428 B2 | 4/2005 | Binette et al. |
| 6,887,270 B2 | 5/2005 | Miller et al. |
| 6,899,729 B1 | 5/2005 | Cox et al. |
| 6,918,927 B2 | 7/2005 | Bates et al. |
| 6,996,952 B2 | 2/2006 | Gupta et al. |
| 7,070,858 B2 | 7/2006 | Shalaby et al. |
| 7,101,381 B2 | 9/2006 | Ford et al. |
| 7,152,611 B2 | 12/2006 | Brown et al. |
| 7,323,189 B2 | 1/2008 | Pathak |
| 7,415,811 B2 | 8/2008 | Gottlieb et al. |
| 8,124,127 B2 | 2/2012 | Faucher et al. |
| 8,263,102 B2 | 9/2012 | Labrecque et al. |
| 8,312,836 B2 | 11/2012 | Corbeil et al. |
| 8,367,099 B2 | 2/2013 | Herweck et al. |
| 2001/0025034 A1 | 9/2001 | Arbiser |
| 2001/0025196 A1 | 9/2001 | Chinn et al. |
| 2001/0051595 A1 | 12/2001 | Lyons et al. |
| 2002/0002154 A1 | 1/2002 | Guivarc'h et al. |
| 2002/0007209 A1 | 1/2002 | Scheerder et al. |
| 2002/0012741 A1 | 1/2002 | Heinz et al. |
| 2002/0026899 A1 | 3/2002 | McLaughlin et al. |

(56) References Cited

U.S. PATENT DOCUMENTS

| | | |
|---|---|---|
| 2002/0026900 A1 | 3/2002 | Huang et al. |
| 2002/0032414 A1 | 3/2002 | Ragheb et al. |
| 2002/0055701 A1 | 5/2002 | Fischell et al. |
| 2002/0098278 A1 | 7/2002 | Bates et al. |
| 2002/0116045 A1 | 8/2002 | Eidenschink |
| 2002/0120333 A1 | 8/2002 | Keogh et al. |
| 2002/0122877 A1 | 9/2002 | Harish et al. |
| 2002/0142089 A1 | 10/2002 | Koike et al. |
| 2002/0193829 A1 | 12/2002 | Kennedy et al. |
| 2003/0003125 A1 | 1/2003 | Nathan et al. |
| 2003/0003221 A1 | 1/2003 | Zhong et al. |
| 2003/0004564 A1 | 1/2003 | Elkins et al. |
| 2003/0055403 A1 | 3/2003 | Nestenborg et al. |
| 2003/0065292 A1 | 4/2003 | Darouiche et al. |
| 2003/0065345 A1 | 4/2003 | Weadock |
| 2003/0069632 A1 | 4/2003 | De Scheerder et al. |
| 2003/0072784 A1 | 4/2003 | Williams |
| 2003/0077272 A1 | 4/2003 | Pathak |
| 2003/0077310 A1 | 4/2003 | Pathak et al. |
| 2003/0077452 A1 | 4/2003 | Guire et al. |
| 2003/0083740 A1 | 5/2003 | Pathak |
| 2003/0086958 A1 | 5/2003 | Arnold et al. |
| 2003/0094728 A1 | 5/2003 | Tayebi |
| 2003/0108588 A1 | 6/2003 | Chen et al. |
| 2003/0130206 A1 | 7/2003 | Koziak et al. |
| 2003/0152609 A1 | 8/2003 | Fischell et al. |
| 2003/0175408 A1 | 9/2003 | Timm et al. |
| 2003/0176915 A1 | 9/2003 | Wright et al. |
| 2003/0181975 A1 | 9/2003 | Ishii et al. |
| 2003/0191179 A1 | 10/2003 | Joshi-Hangal et al. |
| 2003/0204168 A1 | 10/2003 | Bosma et al. |
| 2003/0204618 A1 | 10/2003 | Foster et al. |
| 2003/0207019 A1 | 11/2003 | Shekalim et al. |
| 2003/0211230 A1 | 11/2003 | Pacetti et al. |
| 2003/0220297 A1 | 11/2003 | Berstein et al. |
| 2004/0006296 A1 | 1/2004 | Fischell et al. |
| 2004/0014810 A1 | 1/2004 | Horrobin |
| 2004/0018228 A1 | 1/2004 | Fischell et al. |
| 2004/0039441 A1 | 2/2004 | Rowland et al. |
| 2004/0060260 A1 | 4/2004 | Gottlieb et al. |
| 2004/0071756 A1 | 4/2004 | Fischell et al. |
| 2004/0072849 A1 | 4/2004 | Schreiber et al. |
| 2004/0073284 A1 | 4/2004 | Bates et al. |
| 2004/0131755 A1 | 7/2004 | Zhong et al. |
| 2004/0133275 A1 | 7/2004 | Mansmann |
| 2004/0137066 A1 | 7/2004 | Jayaraman |
| 2004/0137179 A1 | 7/2004 | Matsuda et al. |
| 2004/0142094 A1 | 7/2004 | Narayanan |
| 2004/0146546 A1 | 7/2004 | Gravett et al. |
| 2004/0156879 A1 | 8/2004 | Muratoglu et al. |
| 2004/0161464 A1 | 8/2004 | Domb |
| 2004/0167572 A1 | 8/2004 | Roth et al. |
| 2004/0170685 A1 | 9/2004 | Carpenter et al. |
| 2004/0192643 A1 | 9/2004 | Pressato et al. |
| 2004/0215219 A1 | 10/2004 | Eldridge et al. |
| 2004/0224003 A1 | 11/2004 | Schultz |
| 2004/0230176 A1 | 11/2004 | Shanahan et al. |
| 2004/0234574 A9 | 11/2004 | Sawhney et al. |
| 2004/0241211 A9 | 12/2004 | Fischell |
| 2004/0256264 A1 | 12/2004 | Israelsson et al. |
| 2005/0010078 A1 | 1/2005 | Jamiolkowski et al. |
| 2005/0084514 A1 | 4/2005 | Shebuski et al. |
| 2005/0095267 A1 | 5/2005 | Campbell et al. |
| 2005/0100655 A1 | 5/2005 | Zhong et al. |
| 2005/0106209 A1 | 5/2005 | Ameri et al. |
| 2005/0112170 A1 | 5/2005 | Hossainy et al. |
| 2005/0113849 A1 | 5/2005 | Popadiuk et al. |
| 2005/0129787 A1 | 6/2005 | Murad |
| 2005/0158361 A1 | 7/2005 | Dhondt et al. |
| 2005/0159809 A1 | 7/2005 | Hezi-Yamit et al. |
| 2005/0165476 A1 | 7/2005 | Furst et al. |
| 2005/0165477 A1 | 7/2005 | Anduiza et al. |
| 2005/0182485 A1 | 8/2005 | Falotico et al. |
| 2005/0187376 A1 | 8/2005 | Pacetti |
| 2005/0203635 A1 | 9/2005 | Hunter et al. |
| 2005/0203636 A1 | 9/2005 | McFetridge |
| 2005/0223679 A1 | 10/2005 | Gottlieb et al. |
| 2005/0232971 A1 | 10/2005 | Hossainy et al. |
| 2005/0249775 A1 | 11/2005 | Falotico et al. |
| 2005/0283229 A1 | 12/2005 | Dugan et al. |
| 2006/0008501 A1 | 1/2006 | Dhont et al. |
| 2006/0036311 A1 | 2/2006 | Nakayama et al. |
| 2006/0058881 A1 | 3/2006 | Trieu |
| 2006/0067974 A1 | 3/2006 | Labrecque et al. |
| 2006/0067975 A1 | 3/2006 | Labrecque et al. |
| 2006/0067976 A1 | 3/2006 | Ferraro et al. |
| 2006/0067977 A1 | 3/2006 | Labrecque et al. |
| 2006/0067983 A1 | 3/2006 | Swanick et al. |
| 2006/0068674 A1 | 3/2006 | Dixit et al. |
| 2006/0078586 A1 | 4/2006 | Ferraro et al. |
| 2006/0083768 A1 | 4/2006 | Labrecque et al. |
| 2006/0088596 A1 | 4/2006 | Labrecque et al. |
| 2006/0093643 A1 | 5/2006 | Stenzel |
| 2006/0110457 A1 | 5/2006 | Labrecque et al. |
| 2006/0121081 A1 | 6/2006 | Labrecque et al. |
| 2006/0124056 A1 | 6/2006 | Behnisch et al. |
| 2006/0134209 A1 | 6/2006 | Labhasetwar et al. |
| 2006/0158361 A1 | 7/2006 | Chou |
| 2006/0204738 A1 | 9/2006 | Dubrow et al. |
| 2006/0210701 A1 | 9/2006 | Chappa et al. |
| 2006/0240069 A1 | 10/2006 | Utas et al. |
| 2006/0246105 A1 | 11/2006 | Molz et al. |
| 2007/0015893 A1 | 1/2007 | Hakuta et al. |
| 2007/0071798 A1 | 3/2007 | Herweck et al. |
| 2007/0084144 A1 | 4/2007 | Labrecque et al. |
| 2007/0093894 A1 | 4/2007 | Darouiche |
| 2007/0202149 A1 | 8/2007 | Faucher et al. |
| 2007/0212411 A1 | 9/2007 | Fawzy et al. |
| 2007/0264460 A1 | 11/2007 | Del Tredici |
| 2007/0275074 A1 | 11/2007 | Holm et al. |
| 2007/0280986 A1 | 12/2007 | Gil et al. |
| 2007/0286891 A1 | 12/2007 | Kettlewell et al. |
| 2007/0299538 A1 | 12/2007 | Roeber |
| 2008/0044481 A1 | 2/2008 | Harel |
| 2008/0045557 A1 | 2/2008 | Grainger et al. |
| 2008/0086216 A1 | 4/2008 | Wilson et al. |
| 2008/0109017 A1 | 5/2008 | Herweck et al. |
| 2008/0113001 A1 | 5/2008 | Herweck et al. |
| 2008/0206305 A1 | 8/2008 | Herweck et al. |
| 2008/0279929 A1 | 11/2008 | Devane et al. |
| 2008/0286440 A1 | 11/2008 | Scheer et al. |
| 2008/0289300 A1 | 11/2008 | Gottlieb et al. |
| 2009/0011116 A1 | 1/2009 | Herweck et al. |
| 2009/0047414 A1 | 2/2009 | Corbeil et al. |
| 2009/0181937 A1 | 7/2009 | Faucher et al. |
| 2009/0208552 A1 | 8/2009 | Faucher et al. |
| 2010/0183697 A1 | 7/2010 | Swanick et al. |
| 2010/0209473 A1 | 8/2010 | Dhont et al. |
| 2010/0233232 A1 | 9/2010 | Swanick et al. |
| 2011/0274823 A1 | 11/2011 | Labrecque et al. |
| 2012/0016038 A1 | 1/2012 | Faucher et al. |
| 2012/0213839 A1 | 8/2012 | Faucher et al. |

FOREIGN PATENT DOCUMENTS

| | | |
|---|---|---|
| EP | 0623354 | 11/1994 |
| EP | 0730864 | 9/1996 |
| EP | 0790822 | 8/1997 |
| EP | 0873133 | 10/1998 |
| EP | 0917561 | 5/1999 |
| EP | 1140243 | 10/2001 |
| EP | 1181943 | 2/2002 |
| EP | 1270024 | 1/2003 |
| EP | 1273314 | 1/2003 |
| EP | 1364628 | 11/2003 |
| EP | 1520795 | 4/2005 |
| EP | 1557183 | 7/2005 |
| EP | 2083875 | 8/2009 |
| EP | 1 402 906 | 6/2011 |
| WO | WO 86/00912 | 2/1986 |
| WO | WO 90/01969 | 3/1990 |
| WO | WO 95/26715 | 10/1995 |
| WO | WO 97/02042 | 1/1997 |
| WO | WO 97/09367 | 3/1997 |

(56) References Cited

FOREIGN PATENT DOCUMENTS

| WO | WO 97/13528 | | 4/1997 | |
|---|---|---|---|---|
| WO | WO 98/30206 | | 7/1998 | |
| WO | WO 98/54275 | | 12/1998 | |
| WO | WO 99/25336 | | 5/1999 | |
| WO | WO 00/40278 | | 7/2000 | |
| WO | WO 00/62830 | | 10/2000 | |
| WO | WO 01/24866 | | 4/2001 | |
| WO | WO 01/26585 | | 4/2001 | |
| WO | WO 01/37808 | | 5/2001 | |
| WO | WO 01/60586 | | 8/2001 | |
| WO | WO 01/66036 | | 9/2001 | |
| WO | WO 01/76649 | | 10/2001 | |
| WO | WO 02/49535 | | 6/2002 | |
| WO | WO 02/100455 | | 12/2002 | |
| WO | WO 03/000308 | | 1/2003 | |
| WO | WO 03/015748 | | 2/2003 | |
| WO | WO 03/028622 | | 4/2003 | |
| WO | WO 03/037397 | | 5/2003 | |
| WO | WO 03/037398 | | 5/2003 | |
| WO | WO 03/039612 | * | 5/2003 | .............. A61L 27/54 |
| WO | WO 03/041756 | | 5/2003 | |
| WO | WO 03/070125 | | 8/2003 | |
| WO | WO 03/092741 | | 11/2003 | |
| WO | WO 03/092779 | | 11/2003 | |
| WO | WO 2004/004598 | | 1/2004 | |
| WO | WO 2004/006976 | | 1/2004 | |
| WO | WO 2004/006978 | | 1/2004 | |
| WO | WO 2004/028583 | | 4/2004 | |
| WO | WO 2004/091684 | | 10/2004 | |
| WO | WO 2005/000165 | | 1/2005 | |
| WO | WO 2005/016400 | | 2/2005 | |
| WO | WO 2005/053767 | | 6/2005 | |
| WO | WO 2005/073091 | | 8/2005 | |
| WO | WO 2005/116118 | | 12/2005 | |
| WO | WO 2006/024488 | | 3/2006 | |
| WO | WO-2006/036967 A1 | | 4/2006 | |
| WO | WO 2006/102374 | * | 9/2006 | .............. A61F 13/15 |
| WO | WO 2007/047028 | | 4/2007 | |
| WO | WO 2008/057328 | | 5/2008 | |
| WO | WO 2012/009707 | | 1/2012 | |

OTHER PUBLICATIONS

Autosuture, "Parietex™ Composite OS Series Mesh," retrieved online at http://www.autosuture.com/AutoSuture/pagebuilder.aspx?topicID=135734&breadcrumbs=135 601:0 (2007).
International Search Report for Application No. PCT/US2007/022944, dated Apr. 8, 2009.
International Preliminary Report on Patentability for Application No. PCT/US2007/022944, dated Oct. 14, 2009.
Non-Final Office Action for U.S. Appl. No. 12/401,243 mailed Jan. 5, 2012.
Non-Final Office Action for U.S Appl. 12/182,261 mailed Dec. 21, 2011.
Notice of Allowance for U.S. Appl. No. 11/582,135 mailed Jan. 9, 2012.
Non-Final Office Action for U.S. Appl. No. 12/182,165 mailed Jan. 5, 2012.
Final Office Action for U.S. Appl. No. 11/701,799 mailed Feb. 13, 2012.
Non-Final Office Action for U.S. Appl. No. 11/236,908 mailed Dec. 2, 1201.
Non-Final Office Action for U.S. Appl. No. 12/581,582 mailed Mar. 14, 2012.
Final Office Action for U.S. Appl. No. 12/185,165 mailed Apr. 6, 2012.
Final Office Action for U.S. Appl. No, 12/182,261 mailed Apr. 30, 2012.
Notice of Allowance for U.S. Appl. No. 11/236,908 mailed May 11, 2012.
Final Office Action for U.S. Appl. No. 12/401,243 mailed Jun. 11, 2012,.

"Cure" in Academic Press Dictionary of Science and Technology (1992).
"Polymerization" Merriam-Webster Online Dictionary, retrieved from <www.merriam-webster.com> on Dec. 13, 2009; Merriam-Webster's Inc. 2009; pp. 1.
A paper entitled "Evaluation of the Biocompatibility and Drug Delivery Capabilities of Biological Oil Based Stent Coatings" by Shengqio Li of the Katholieke Universiteit Leuven.
Ahuja et al. Journal of Indian Pediatric Surgery 2002 7:15-20.
Camurus, "In our endeavors to create the unique, we start with the best. Your product."
De Scheerder, Ivan K. et al. "Biocompatibility of polymer-coated oversized metallic stents implanted in normal porcine coronary arteries," Atherosclerosis, vol. 114:105-114.
Drummond, Calum J. et al., "Surfactant self-assembly objects as novel drug delivery vehicles," Current Opinion in Colliod & Interface Science, vol. 4:449-456 (2000).
Engstrom, Sven, "Drug Delivery from Cubic and Other Lipid-water Phases," Lipid Technology, vol. 2(2):42-45 (1990).
Guler, et al. "Some empirical equations for oxopolymerization of linseed oil," Progress in Organic Coatings, vol. 51:365-371 (2004).
Hwang, Chao-Wei et al, "Physiological Transport Forces Govern Drug Distribution for Stent-Based Delivery," Circulation, vol. 104:600-605 (2001).
Jonasson, Lena et al., "Cyclosporon A inhibits smooth muscle proliferation in the vascular response to injury," Proc. Natl. Acad. Sci. USA, vol. 85: 2303-2306 (1988).
Mallegol et al., "Drier Influence on the Curing of Linseed Oil," Progress in Organic Coatings 39:107-113 (2000).
Morse, Richard "Molecular Distillation of Polymerized Drying Oils," Industrial and Engineering Chemisry 33:1039-1043 (1941).
Oberhoff, Martin et al, "Local and Systemic Delivery of Low Molecular Weight Heparin Following PTCA: Acute Results and 6-Month Follow-Up of the Initial Clinical Experience With the Porous Balloon (PILOT-Study)," Catheterization and Cardiovascular Diagnosis, vol. 44:267-274 (1998).
Ogunniyi, D.S., "Castor oil: A vital industrial raw material," Biosource Technology, vol. 97: 1086-1091 (2006).
Redman, L.V. et al., "The drying rate of raw paint oils—a comparison," The Journal of Industrial and Engineering Chemistry, vol. 5: 630-636 (1913).
Salu, Koen J. et al, "Addition of cytochalasin D to a biocompatible oil stent coating inhibits intimal hyperplasia in a porcine coronary model," Coronary Artery Disease, vol. 14(8):545-555 (2003).
Scheller, Bruno et al, "Addition of Paclitaxel to Contrast Media Prevents Restenosis After Coronary Stent Implantation," Journal of the American College of Cardiology, vol. 42(8):1415-1420 (2003).
Shahidi, Fereidoon ed.; "Bailey's Industrial Oil and Fats Products" 2005; John Wiley and Sons; vol. 5, Edible Oil and Fat Products: Processing Technologies, pp. 1-15.
Van der Giessen, Willem J. et al, "Marked Inflammatory Sequelae to Implantation of Biodegradable and Nonbiodegradable Polymers in Porcine Coronary Arteries," Circulation, vol. 94:1690-1697 (1996).
Websters Dictionary Online, Accessed on Feb. 13, 2009, entry for "polymer" p. 1 of 1.
Binder et al., "Chromatographic Analysis of Seed Oils. Fatty Acid Composition of Castor Oil," The Journal of the American Oil Chemists' Society, vol. 39:513-517 (1962).
CECW-EE, "Ch. 4: Coating Types and Characteristics," Engineering and Design—Painting: New Construction and Maintenance, pp. 4-1 to 4-24 (1995).
Wikipedia, "Sirolimus," pp. 1-13, available online at http://en.wikipedia.org/wiki/Sirolimus, date accessed May 11, 2011.
Timir-Balizsy et al., "Chemical Principals of Textile Conservation," Oxford: Elsevier Science Ltd., 1998:117-119.
Crivello et al., "Epoxidized triglycerides as renewable monomers in photoinitiated cationic polymerization," Chem. Mater, 1992:692-699.
International Search Report for International Application PCT/US05/034601, dated Apr. 10, 2006.
International Search Report for International Application PCT/US05/034610, dated Mar. 16, 2006.

(56) References Cited

OTHER PUBLICATIONS

International Search Report for International Application PCT/US05/034614, dated Aug. 29, 2006.
International Search Report for International Application PCT/US05/034615, dated May 16, 2006.
International Search Report for International Application PCT/US05/034678, dated Aug. 28, 2006.
International Search Report for International Application PCT/US05/034681, dated Jul. 26, 2006.
International Search Report for International Application PCT/US05/034682, dated Jul. 20, 2006.
International Search Report for International Application PCT/US05/034836, dated Jul. 6, 2006.
International Search Report for International Application PCT/US05/034941, dated May 4, 2006.
International Search Report for International Application PCT/US06/037184, dated Feb. 22, 2007.
International Preliminary Report on Patentability for International Application PCT/US06/040753, dated Oct. 3, 2008.
International Search Report for International Application PCT/US06/040753, dated Sep. 24, 2007.
International Search Report for International Application PCT/US07/019978, dated May 7, 2009.
International Search Report for International Application PCT/US07/022860, dated Apr. 22, 2009.
International Search Report for International Application PCT/US08/000565, dated May 4, 2009.
International Preliminary Examination Report for International Application PCT/US08/071547, dated Aug. 26, 2010.
International Search Report for International Application PCT/US08/071547, dated Oct. 22, 2008.
International Preliminary Report on Patentability for International Application PCT/US08/071565, dated Aug. 27, 2009.
International Search Report for International Application PCT/US08/071565, dated Nov. 10, 2008.
International Search Report for International Application PCT/US08/085386, dated Feb. 4, 2009.
International Search Report for International Application PCT/US09/037364, dated Aug. 27, 2009.
International Search Report for International Application PCT/US10/026521, dated Jun. 23, 2010.
International Search Report for International Application PCT/US10/052899, dated Jan. 10, 2011.
Supplementary European Search Report in Application No. EP 05 80 4291, dated Jul. 26, 2011.
Supplementary European Search Report for Application No. EP 05 80 2894, dated Jul. 27, 2011.
Supplementary European Search Report in Application No. 05 800 844, dated Aug. 19, 2011.
Supplementary European Search Report in Application No. EP 05 85 8430, dated Aug. 18, 2011.
Non-final Office Action for U.S. Appl. No. 11/236,908, mailed Mar. 25, 2006.
Final Office Action for U.S. Appl. No. 11/236,908, mailed May 17, 2011.
Non-final Office Action for U.S. Appl. No. 11/236,908, mailed Aug. 24, 2009.
Final Office Action for U.S. Appl. No. 11/236,943, mailed Dec. 23, 2009.
Non-Final Office Action for U.S. Appl. No. 11/236,943, mailed Mar. 5, 2009.
Non-final Office Action for U.S. Appl. No. 11/236,977, mailed Aug. 3, 2009.
Final Office Action for U.S. Appl. No. 11/237,263, mailed Jul. 7, 2010.
Non-final Office Action for U.S. Appl. No. 11/237,263, mailed Oct. 7, 2009.
Final Office Action for U.S. Appl. No. 11/237,264, mailed Jun. 2, 2010.
Non-final Office Action for U.S. Appl. No. 11/237,264, mailed Oct. 5, 2009.
Final Office Action for U.S. Appl. No. 11/701,799, mailed Nov. 23, 2010.
Non-final Office Action for U.S. Appl. No. 11/237,420, mailed Mar. 5, 2009.
Final Office Action for U.S. Appl. No. 11/237,420, mailed Nov. 4, 2009.
Non-final Office Action for U.S. Appl. No. 11/237,420, mailed Dec. 6, 2010.
Non-final Office Action for U.S. Appl. No. 11/238,532, mailed Mar. 30, 2009.
Final Office Action for U.S. Appl. No. 11/238,532, mailed Sep. 9, 2009.
Final Office Action for U.S. Appl. No. 11/238,554, mailed May 12, 2010.
Non-final Office Action for U.S. Appl. No. 11/238,554, mailed Oct. 9, 2009.
Final Office Action for U.S. Appl. No. 11/238,554, mailed May 1, 2009.
Non-final Office Action for U.S. Appl. No. 11/238,554, mailed Jul. 25, 2008.
Non-final Office Action for U.S. Appl. No. 11/238,564, mailed Apr. 16, 2008.
Final Office Action for U.S. Appl. No. 11/238,564, mailed Aug. 6, 2009.
Non-final Office Action for U.S. Appl. No. 11/239,555, mailed Mar. 30, 2009.
Non-final Office Action for U.S. Appl. No. 11/525,328, mailed Apr. 30, 2007.
Non-final Office Action for U.S. Appl. No. 11/525,390, mailed Jul. 14, 2010.
Final Office Action for U.S. Appl. No. 11/525,390, mailed Feb. 21, 2011.
Final Office Action for U.S. Appl. No. 11/582,135, mailed May 12, 2011.
Non-final Office Action for U.S. Appl. No. 11/582,135, mailed Nov. 9, 2010.
Non-final Office Action for U.S. Appl. No. 11/582,135, mailed Jan. 6, 2010.
Non-final Office Action for U.S. Appl. No. 11/582,135, mailed May 12, 2009.
Non-final Office Action for U.S. Appl. No. 11/701,799, mailed Apr. 12, 2010.
Non-final Office Action for U.S. Appl. No. 11/980,155, mailed Mar. 24, 2011.
Non-final Office Action for U.S. Appl. No. 12/075,223, mailed Dec. 8, 2010.
Non-final Office Action for U.S. Appl. No. 12/325,546, mailed Feb. 25, 2010.
Final Office Action for U.S. Appl. No. 12/325,546, mailed Aug. 31, 2010.
Non-final Office Action for U.S. Appl. No. 12/364,763, mailed Dec. 11, 2009.
Final Office Action for U.S. Appl. No. 12/364,763, mailed Sep. 21, 2010.
Interview summary for U.S. Appl. No. 11/236,908 mailed May 5, 2009.
Interview summary for U.S. Appl. No. 11/236,908 mailed Dec. 2, 2010.
Interview summary for U.S. Appl. No. 11/237,420 mailed May 5, 2009.
Interview summary for U.S. Appl. No. 11/582,135 mailed Dec. 7, 2010.
Interview summary for U.S. Appl. No. 12/325,546 mailed Dec. 2, 2010.
Interview summary for U.S. Appl. No. 12/364,763 mailed Dec. 2, 2010.
Non-final Office Action for U.S. Appl. No. 11/525,390, mailed Jul. 11, 2011.
Final Office Action for U.S. Appl. No. 11/237,420 , mailed Jul. 13, 2011.

(56) References Cited

OTHER PUBLICATIONS

Final Office Action for U.S. Appl. No. 12/075,223, mailed Aug. 11, 2011.
Non-Final Office Action for U.S. Appl. No. 11/701,799, mailed Aug. 17, 2011.
Non-Final Office Action for U.S. Appl. No. 11/582,135, mailed Oct. 14, 2011.
Final Office Action for U.S. Appl. No. 11/980,155, mailed Oct. 21, 2011.
Ackman, R.G., "Fish Oils", *Bailey's Industrial Oil and Fat Products*, 6th Edition, 279-317 (2005).
Andes, et al. "Antiproliferative Strategies for the Treatment of Vascular Proliferative Disease", *Current Vascular Pharmacology*, 1)1): 85-98 (2003).
Rutkow, Ira M. et al., "'Tension-free' inguinal herniorrhaphy: A preliminary report on the 'mesh plug' technique," Surgery, vol. 114:3-8 (1993).
Winter, et al., "Physical and Chemical Gelation" *Encyclopedia of Materials—Science and Technology*, vols. 1-11: 6691-6999 (2001).
International Search Report for International Application No. PCT/US05/34941, dated May 4, 2006.
International Search Report for PCT/US2011/44292, dated Dec. 6, 2011.
Supplementary European Search Report for EP 08782511, dated Apr. 16, 2013.
Notice of Allowance for U.S. Appl. No. 12/182,261, mailed Jul. 23, 2012.
Supplementary European Search Report for Application No. EP 08877338.7, dated Aug. 16, 2012.
Supplementary European Search Report for Application No. EP09819594.4, dated Aug. 14, 2012.
Supplementary European Search Report for Application No. EP 12004057, dated Apr. 10, 2013.
Advisory Action for U.S. Appl. No. 12/401,243, mailed Aug. 27, 2012.
Final Office Action for U.S. Appl. No. 12/581,582 mailed Aug. 29, 2012.
Notice of Allowance for U.S. Appl. No. 11/525,390, mailed Oct. 4, 2012.
Advisory Action for U.S. Appl. No. 12/581,582, dated Nov. 14, 2012.
Notice of Allowance for U.S. Appl. No. 11/525,390, dated Nov. 20, 2012.
Non-Final Office Action for U.S. Appl. No. 13/404,487, dated Dec. 20, 2012.
Non-Final Office Action for U.S. Appl. No. 13/184,512, dated Jan. 31, 2013.
Non-Final Office Action for U.S. Appl. No. 13/682,991, dated Mar. 18, 2013.
Notice of Allowance for U.S. Appl. No. 13/404,487, dated Apr. 2, 2013.
Non-Final Office Action for U.S. Appl. No. 11/236,943, dated Apr. 22, 2013.

\* cited by examiner

COATED SURGICAL MESH

RELATED APPLICATIONS

This application claims priority to, and the benefit of, co-pending U.S. Provisional Application 60/856,983, filed Nov. 6, 2006, for all subject matter common to both applications. The disclosure of said provisional application is hereby incorporated by reference in its entirety.

FIELD OF THE INVENTION

The present invention relates to implantable devices forming tissue separating layer, and more particularly to a soft tissue device, such as a coated surgical mesh, that is able to deliver therapeutic agents to a targeted location and makes use of a coating promoting modulated healing.

BACKGROUND OF THE INVENTION

Biocompatible medical films are most often used in surgical settings as a physical barrier to help separate certain organs from adjacent tissues and medical devices following surgical intervention or blunt dissection to minimize adhesion formation. For example, Seprafilm®, a product of Genzyme Corporation of Cambridge, Mass., is used in patients undergoing abdominal or pelvic laparotomy as an adjunct intended to reduce the incidence, extent, and severity of post-operative adhesions between different tissues and organs and implantable medical devices such as soft tissue support membranes and mesh.

U.S. Pat. No. 5,017,229 is directed to a water insoluble, biocompatible gel that includes the reaction product of hyaluronic acid, a polyanionic polysaccharide, and an activating agent. The gel described in the '229 patent can be provided in the form of an adhesion prevention composition, such as a membrane or composition suitable for incorporation into a syringe. The gel is described as being able to form a film by being compressed or allowed to dehydrate. When modified with polysaccharide, the film forms the above-described Seprafilm® anti-adhesion or adhesion barrier product.

However, such commercially available adhesion prevention and adhesion barrier products often are difficult to handle and apply to the targeted location due to their chemical make up and bio-dissolvable properties. The composition and structural properties of these bio-dissolvable products require that they be handled with dry hands or instruments, which can be difficult during most surgical intervention operations. Furthermore, many of these bio-dissolvable films are made intentionally to be thin to minimize tissue disruption and consequently end up being structurally weak (i.e., easily torn or folded during handling).

Surgical meshes, which are used to reinforce weakened areas of abdominal, pelvic, or thoracic tissues, or to replace a portion of internal structural soft tissue that has neither been damaged nor removed surgically, can also be made to have anti-adhesion properties. PCT Application Publication No. WO 2004/028583 is directed to compositions, devices, and methods for maintaining or improving the integrity of body passageways following surgery or injury. Surgical mesh drug eluting delivery devices can include one or more therapeutic agents provided with a drug eluting mesh wrap implant placed adjacent to medical devices and internal tissue as described therein. The meshes are available in various single layer, multi-layer, and 3-dimensional configurations made without bioabsorbable adhesion coatings and films. The meshes are most often constructed of synthetic non-absorbable polymer materials, such as polyethylene, polytetrafluoroethylene, and polypropylene, and can include a carrier having a therapeutic agent attached thereto, incorporated within, or coated thereon. The mesh structure for this surgical application serves as a drug eluting delivery apparatus for local therapeutic delivery within the body. Affixing the carrier and or coating directly onto the surgical mesh makes it easier to handle the device without the drawbacks of film, namely tearing, folding, and rapid dissolving when contacting body fluids, and the lack of fixation or anchoring means. Non-absorbable mesh structures generally provide more handling strength and directional placement control during installation than bio-absorbable or bio-dissolvable polymer films.

PCT Application Publication No. WO 03/028622 is directed to film and mesh devices that include therapeutic agents in combination with the anti-adhesion properties and, as well as a method of delivering drugs to a tissue using drug coated medical devices. The drug coated medical device is brought into contact with the target tissue or circulation and the drugs are quickly released onto the area surrounding the device in a short period of time after contact is made. The release of the drug may occur over a period of 30 seconds, 1 minute or 3 minutes. In one embodiment described in the publication, the carrier of the drug is a liposome. Other particles described as potential drug carriers include lipids, sugars, carbohydrates, proteins, and the like. The publication describes these carriers as having properties appropriate for a quick short term release of a drug combined with the carriers.

SUMMARY OF THE INVENTION

There is a need for a coated surgical mesh, with or without the ability to deliver therapeutic agents, but having a structure predisposed to promoting tissue in-growth and providing adhesion-limiting characteristics, with one or more surfaces that modulate healing, and limit or reduce the degree of adhesion formation with adjacent tissues and/or other medical devices. The present invention is directed toward further solutions to address this need.

In accordance with aspects of the present invention, the coated surgical mesh is in the form of a biocompatible mesh structure composed of a plurality of inter-coupled strands forming a plurality of interstices therebetween.

In accordance with aspects of the present invention, a coated medical surgical is provided, composed of a biocompatible mesh structure composed of a plurality of inter-coupled strands forming a plurality of interstices therebetween; and a coating derived from fish oil, which can additionally include vitamin E, wherein said coating encapsulates the strands while maintaining the plurality of interstices uncoated.

In accordance with aspects of the present invention, a method of making a coated surgical mesh is provided, the method comprising: providing a biocompatible mesh structure composed of a plurality of inter-coupled strands forming a plurality of interstices therebetween; preparing a coating derived from an oil, such as fish oil; and applying the coating to the biocompatible mesh structure, wherein the coating encapsulates the strands while maintaining spaces of the plurality of interstices uncoated.

In accordance with further aspects of the present invention, the coating additionally includes vitamin E. The coating can be in at least a partially cured state prior to application of the coating on the mesh. The coating may also be subjected to curing conditions subsequent to application of the coating on the mesh, such that the coating is resident on the mesh in at least a partially cured state. Curing with respect to the present invention generally refers to thickening, hardening, or drying of a material brought about by heat, UV light, chemical means, and/or reactive gasses.

In further aspects of the present invention, the biocompatible mesh structure is treated prior to application of the coating. Suitable pretreatments include, but are not limited to, plasma etching. Pretreatment of the biocompatible mesh structure prior to coating may improve the adhesive forces between the coating and the mesh, diminish coating flow and pooling and/or provide a more continuous coating.

In further aspects of the present invention, the coating and the biocompatible mesh structure may be packaged and sterilized. The step of sterilizing may be performed by vaporized hydrogen peroxide, ethylene oxide (ETO) gas, radiation using gamma or electron-beam radiation, steam and gas plasma.

In accordance with further aspects of the present invention, the coating includes at least one therapeutic agent. The therapeutic agent can include an agent selected from the group consisting of antioxidants, anti-inflammatory agents, anticoagulant agents, drugs to alter lipid metabolism, anti-proliferatives, anti-neoplastics, tissue growth stimulants, functional protein/factor delivery agents, anti-infective agents, imaging agents, anesthetic agents, chemotherapeutic agents, tissue absorption enhancers, anti-adhesion agents, germicides, analgesics, prodrugs, and antiseptics.

BRIEF DESCRIPTION OF THE DRAWINGS

The aforementioned features and advantages, and other features and aspects of the present invention, will become better understood with regard to the following description and accompanying drawings, wherein.

DETAILED DESCRIPTION

Figure 1:
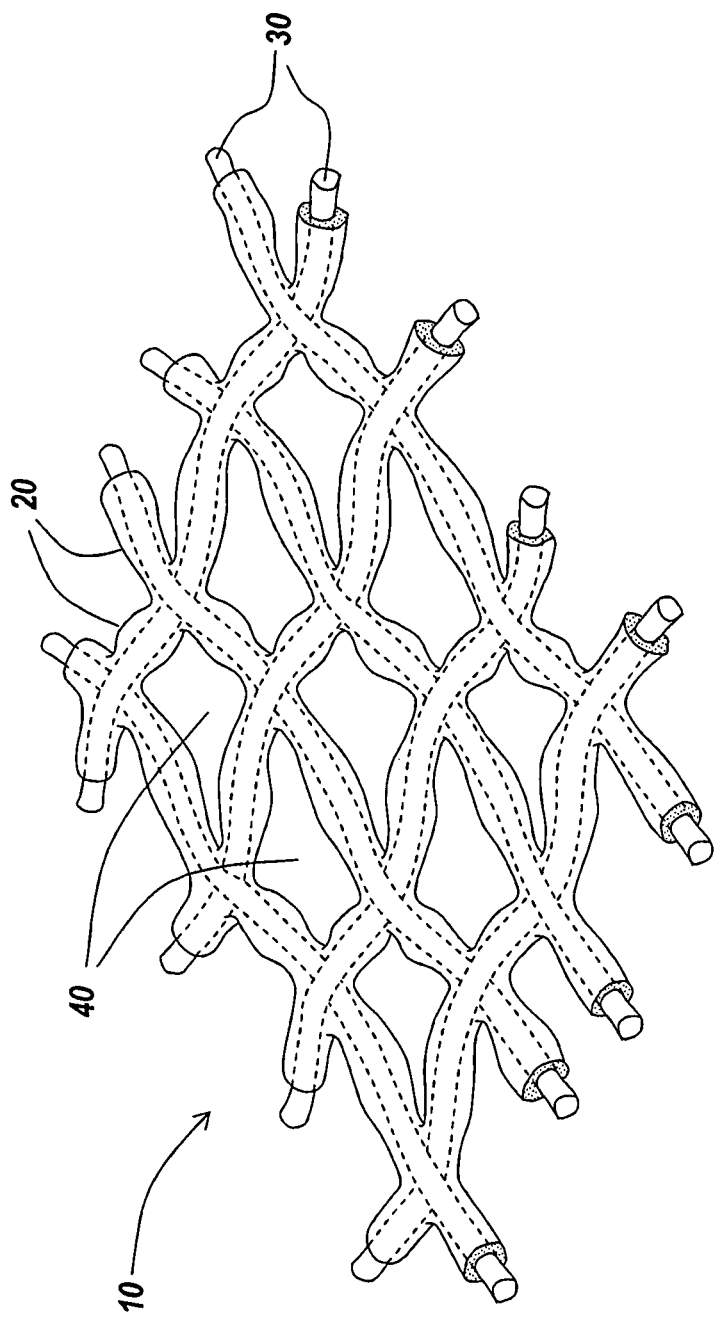
FIG. 1 is a diagrammatic illustration of a coated biocompatible mesh structure, according to one embodiment of the present invention.
Figure 2:
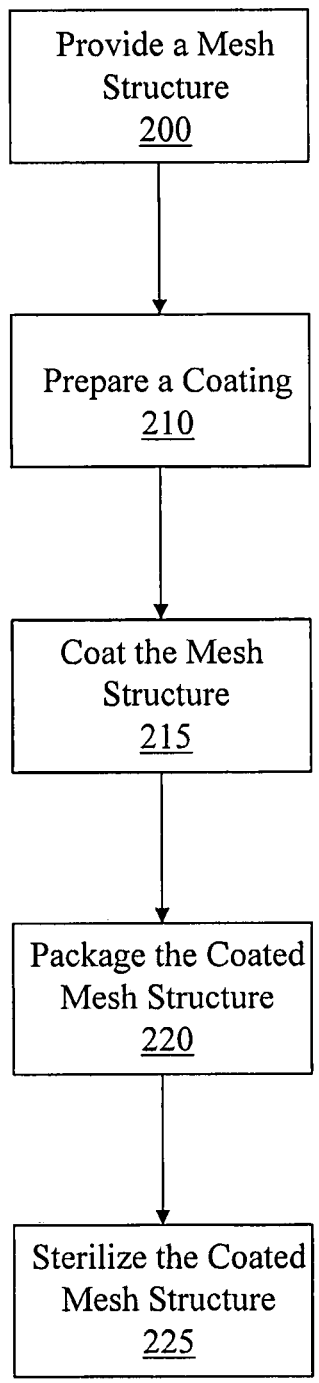
FIG. 2 is a flow chart illustrating a method of making the coated mesh structure of the present invention, in accordance with one embodiment of the present invention.

An illustrative embodiment of the present invention relates to the provision of a coated surgical mesh that can exhibit modulated healing properties, anti-inflammatory properties, non-inflammatory properties and/or anti-adhesion properties, and corresponding method of making. The coated surgical mesh can be its own medical device (i.e., a biocompatible mesh structure), or the coated surgical mesh can be combined with another medical device to provide anti-adhesion characteristics, in addition to improved healing and delivery of therapeutic agents. The coated surgical mesh is generally formed of a biocompatible mesh structure composed of a plurality of inter-coupled strands forming a plurality of interstices therebetween; and a coating derived from an oil, which may additionally include vitamin E, such that the coating encapsulates the strands while maintaining spaces of the plurality of interstices. In addition, the coating can include a therapeutic agent, such as a drug or other bioactive agent. The coated medical device is implantable in a patient for short term or long term applications, and can include controlled release of the therapeutic agent. In one embodiment, the coating derived from fish oil and/or is a non-polymeric, bioabsorbable cross-linked gel.

As utilized herein, the term "bio-absorbable" generally refers to having the property or characteristic of being able to penetrate the tissue of a patient's body. In certain embodiments of the present invention bio-absorption occurs through a lipophilic mechanism. The bio-absorbable substance is soluble in the phospholipid bi-layer of cells of body tissue, and therefore impacts how the bio-absorbable substance penetrates into the cells.

It should be noted that a bio-absorbable substance is different from a biodegradable substance. Biodegradable is generally defined as capable of being decomposed by biological agents, or capable of being broken down by microorganisms or biological processes, in a manner that does not result in cellular uptake of the biodegradable substance. Biodegradation thus relates to the breaking down and distributing of a substance through the patient's body, verses the penetration of the cells of the patient's body tissue. Biodegradable substances, such as polymers, can cause inflammatory response due to either the parent substance or those substances formed during breakdown, and they may or may not be absorbed by tissues. Bio-absorbable substances break down into substances or components that do not cause an inflammatory response and can be consumed by the cells forming the body tissues.

As utilized herein, the term "biocompatible" generally refers having the property or characteristic of not generating injury, toxicity or immunological reaction to living tissues. Accordingly, the coated surgical mesh does not substantively provoke injury, toxicity or an immunological reaction, such as a foreign body reaction or inflammatory response, upon implantation of the medical device in a subject.

The phrases "controlled release" and "released in a controlled manner" generally refer to the release of a therapeutic agent in a predictable manner over the time period of days, weeks or months, as desired and predetermined upon formation of the therapeutic agent on the medical device from which it is being released. Controlled release includes the provision of an initial burst of release upon implantation, followed by the predictable release over the aforementioned time period. Accordingly, controlled release includes such embodiments as those that release substantially all or a significant portion of the therapeutic agent in a predictable manner and a substantially lesser amount of the therapeutic agent for a duration thereafter. Additional embodiments include delivery of a therapeutic agent to a targeted location along with the bioabsorbable components of the coating at the cellular level.

It should be noted that the phrase "cross-linked gel," as utilized herein with reference to the present invention, refers to a gel that is non-polymeric and is derived from an oil composition comprising molecules covalently cross-linked into a three-dimensional network by one or more of ester, ether, peroxide, and carbon-carbon bonds in a substantially random configuration that can reversibly convert into oil compounds. In various preferred embodiments, the oil composition comprises a fatty acid molecule, a glyceride, and combinations thereof. In one embodiment, the oil composition comprises fish oil and may additionally include vitamin E.

Modulated healing can be described as the in-vivo effect observed post-implant in which the biological response is altered resulting in a significant reduction in foreign body response. As utilized herein, the phrase "modulated healing" and variants of this language generally refers to the modulation (e.g., alteration, delay, retardation, reduction, detaining) of a process involving different cascades or sequences of naturally occurring tissue repair in response to localized tissue injury, substantially reducing their inflammatory effect. Modulated healing encompasses many different biologic processes, including epithelial growth, fibrin deposition, platelet activation and attachment, inhibition, proliferation and/or differentiation, connective fibrous tissue production and function, angiogenesis, and several stages of acute and/or chronic inflammation, and their interplay with each other. For example, the bio-absorbable oils described herein can alter, delay, retard, reduce, and/or detain one or more of the phases associated with healing of vascular injury caused by medical procedures, including, but not limited to, the inflammatory phase (e.g., platelet or fibrin deposition), and the proliferative phase. In one embodiment, "modulated healing" refers to the ability of a non-polymeric bio-absorbable cross-linked gel to alter a substantial inflammatory phase (e.g., platelet or fibrin deposition) at the beginning of the tissue healing process. As used herein, the phrase "alter a substantial inflammatory phase" refers to the ability of the non-polymeric bio-absorbable cross-linked gel to substantially reduce the inflammatory response at an injury site. In such an instance, a minor amount of inflammation may ensue in response to tissue injury, but this level of inflammation response, e.g., platelet and/or fibrin deposition, is substantially reduced when compared to inflammation that takes place in the absence of the non-polymeric bio-absorbable cross-linked gel.

For example, the non-polymeric bio-absorbable cross-linked gel of the present invention has been shown experimentally in animal models to delay or alter the inflammatory response associated with vascular injury, as well as excessive formation of connective fibrous tissue following tissue injury. The non-polymeric bio-absorbable cross-linked gel of the present invention has also been shown experimentally in animal models to delay or reduce fibrin deposition and platelet attachment to a blood contact surface following vascular injury. Additionally, experiments have shown that the non-polymeric bio-absorbable cross-linked gel of the present invention has resulted in a less dense, but uniformly confluent cellular overgrowth of a porous implanted mesh structure with little to no fibrous capsule formation.

Accordingly, the non-polymeric bio-absorbable cross-linked gel of the present invention provides an excellent absorbable cellular interface suitable for use with a surgical instrument or medical device that results in a modulated healing effect, avoiding the generation of scar tissue and promoting the formation of healthy tissue at a modulated or delayed period in time following the injury. Without being bound by theory, this modulated healing effect can be attributed to the modulation (e.g., alteration, delay, retardation, reduction, detaining) of any of the molecular processes associated with the healing processes of vascular injury. For example, the non-polymeric bio-absorbable cross-linked gel of the present invention can act as a blocking coating for the surgical mesh, vessel, and the cells and proteins involved in the healing processes of vascular injury. The coating prevents or blocks the interaction between the surgical mesh and the vessel surface, thereby preventing the initiation of the healing process by the cells and proteins of the tissue and blood vessels. In one respect, the coating acts as a patch that binds to the vessel wall and blocks cells and proteins of the vessel wall from recognizing the surgical mesh (i.e., the coating blocks cell-mesh and/or protein-mesh interactions), thereby blocking the initiation of the vascular healing process, and avoiding the fibrin activation and deposition and platelet activation and deposition.

In another non-binding example, the modulated healing effect can be attributed to the modulation (e.g., alteration, delay, retardation, reduction, detaining) of signaling between the cells and proteins that compose the tissue that would otherwise initiate the vascular healing process. Stated differently, at the site of tissue injury, the non-polymeric bio-absorbable cross-linked gel of the present invention can modulate the interaction of cells of the tissue, such as endothelial cells and/or smooth muscle cells, with other cells and/or proteins of the blood that would otherwise interact with the damaged cells to initiate the healing process. Additionally, at the site of tissue injury, the non-polymeric bio-absorbable cross-linked gel of the present invention can modulate the interaction of proteins of the tissue with other cells and/or proteins of the blood, thereby modulating the healing process.

When the non-polymeric bio-absorbable cross-linked gel of the present invention is being used as a coating for a surgical mesh, and the cells and proteins that compose the tissue wall, the bio-absorbable cross-linked gel can be designed to maintain its integrity for a desired period of time, and then begin to dissolve and be absorbed into the tissue that it is surrounded by. Alternatively, the bio-absorbable cross-linked gel can be designed such that, to some degree, it is absorbed into surrounding tissue immediately after the medical device implant is inserted in the subject. Depending on the formulation of the non-polymeric bio-absorbable cross-linked gel that makes up the coating, the coating is completely absorbed into surrounding tissue within a time period of 1 day to 24 months, e.g., 1 week to 12 months, e.g., 1 month to 10 months, e.g., 3 months to 6 months. Animal studies have shown resorption of the coating occurring upon implantation and continuing over a 3 to 6 month period, and beyond.

The oil component of the non-polymeric bio-absorbable cross-linked gel present invention can be either an oil, or an oil composition. The oil component can be a naturally occurring oil, such as fish oil, cod liver oil, cranberry oil, or other oils having desired characteristics. One example embodiment of the present invention makes use of a fish oil in part because of the high content of omega-3 fatty acids, which provide healing support for damaged tissue, as discussed below. The fish oil also serves as an adhesion-limiting agent. In addition, the fish oil maintains anti-inflammatory, non-inflammatory, or "modulated healing" properties as well. The present invention is not limited to the use of fish oil as the naturally occurring oil for the non-polymeric bio-absorbable cross-linked gel. However, the description herein makes reference to the use of fish oil as one example embodiment. Other naturally occurring oils can be utilized in accordance with the present invention as described herein.

To understand further how the non-polymeric bio-absorbable cross-linked gel of the present invention functions, a brief discussion is provided below concerning tissue injury and healing generally.

Wound healing upon vascular injury, and generally in non-vascular locations, occurs in several stages. The first stage is the inflammatory phase. The inflammatory phase is characterized by hemostasis and inflammation. Collagen exposed during wound formation activates the clotting cascade (both the intrinsic and extrinsic pathways), initiating the inflammatory phase. After injury to tissue occurs, the cell membranes, damaged from the wound formation, release thromboxane A2 and prostaglandin 2-alpha, which are potent vasoconstrictors. This initial response helps to limit hemorrhage. After a short period, capillary vasodilatation occurs secondary to local histamine release, and the cells of inflammation are able to migrate to the wound bed. The timeline for cell migration in a normal wound healing process is predictable. Platelets, the first response cells, release multiple chemokines, including epidermal growth factor (EGF), fibronectin, fibrinogen, histamine, platelet-derived growth factor (PDGF), serotonin, and von Willebrand factor. These factors help stabilize the wound through clot formation. These mediators act to control bleeding and limit the extent of injury. Platelet degranulation also activates the complement cascade, specifically C5a, which is a potent chemoattractant for neutrophils.

As the inflammatory phase continues, more immune response cells migrate to the wound. The second response cell to migrate to the wound, the neutrophil, is responsible for debris scavenging, complement-mediated opsonization of bacteria, and bacteria destruction via oxidative burst mechanisms (i.e., superoxide and hydrogen peroxide formation). The neutrophils kill bacteria and decontaminate the wound from foreign debris.

The next cells present in the wound are the leukocytes and the macrophages (monocytes). The macrophage, referred to as the orchestrator, is essential for wound healing. Numerous enzymes and cytokines are secreted by the macrophage. These include collagenases, which debride the wound; interleukins and tumor necrosis factor (TNF), which stimulate fibroblasts (produce collagen) and promote angiogenesis; and transforming growth factor (TGF), which stimulates keratinocytes. This step marks the transition into the process of tissue reconstruction, i.e., the proliferative phase.

The second stage of wound healing is the proliferative phase. Epithelialization, angiogenesis, granulation tissue formation, and collagen deposition are the principal steps in this anabolic portion of wound healing. Epithelialization occurs early in wound repair. At the edges of wounds, epidermis immediately begins thickening. Marginal basal cells begin to migrate across the wound along fibrin strands stopping when they contact each other (contact inhibition). Within the first 48 hours after injury, the entire wound is epithelialized. Layering of epithelialization is re-established. The depths of the wound at this point contain inflammatory cells and fibrin strands. Aging effects are important in wound healing as many, if not most, problem wounds occur in an older population. For example, cells from older patients are less likely to proliferate and have shorter life spans and cells from older patients are less responsive to cytokines.

Chronic inflammation, or granulomatous inflammation, can cause further complications during the healing of vascular, and non-vascular, injury. Granulomas are aggregates of particular types of chronic inflammatory cells which form nodules in the millimeter size range. Granulomas may be confluent, forming larger areas. Essential components of a granuloma are collections of modified macrophages, termed epithelioid cells, usually with a surrounding zone of lymphocytes. Epithelioid cells are so named by tradition because of their histological resemblance to epithelial cells, but are not in fact epithelial; they are derived from blood monocytes, like all macrophages. Epithelioid cells are less phagocytic than other macrophages and appear to be modified for secretory functions. The full extent of their functions is still unclear. Macrophages in granulomas are commonly further modified to form multinucleate giant cells. These arise by fusion of epithelioid macrophages without nuclear or cellular division forming huge single cells which may contain dozens of nuclei. In some circumstances the nuclei are arranged round the periphery of the cell, termed a Langhans-type giant cell; in other circumstances the nuclei are randomly scattered throughout the cytoplasm (i.e., the foreign body type of giant cell which is formed in response to the presence of other indigestible foreign material in the tissue). Areas of granulomatous inflammation commonly undergo necrosis.

Formation of granulomatous inflammation seems to require the presence of indigestible foreign material (derived from bacteria or other sources) and/or a cell-mediated immune reaction against the injurious agent (type IV hypersensitivity reaction).

Compounds that move too rapidly through a tissue may not be effective in providing a sufficiently concentrated dose in a region of interest. Conversely, compounds that do not migrate in a tissue may never reach the region of interest. Cellular uptake enhancers such as fatty acids and cellular uptake inhibitors such as alpha and gamma-tocopherols can be used alone or in combination to provide an effective transport of a given compound to a given cell target, region, or specific tissue location.

As described previously, the process of modulated healing and cellular remodeling with non-polymeric bio-absorbable cross-linked gels involves different cascades or sequences of naturally occurring tissue repair in response to localized tissue injury, and it encompasses many different biologic processes, including epithelial growth, inhibition, proliferation and/or differentiation, connective fibrous tissue production and function, angiogenesis, and several stages of acute and/or chronic inflammation. Therefore, for example, by using the non-polymeric bio-absorbable cross-linked gel of the invention, which has modulated healing characteristics, one or more of the cascades or sequences of naturally occurring tissue repair are modulated (e.g., delayed), resulting in long-term stabilization of the areas treated by, for example, the non-polymeric bio-absorbable cross-linked gel-coated devices. The reversibly cross-linked gel has been shown experimentally in animal models not to produce or induce a protracted inflammatory response and to delay healing or formation of connective fibrous tissue following tissue injury. As such, the non-polymeric bio-absorbable cross-linked gel of the present invention can delay fibrin and platelet activation associated with the initial phase of wound healing, and this delay will result in a lower long-term risk of tissue injury due to the formation of vulnerable plaques associated with the initial fibrin and platelet activation. Accordingly, the non-polymeric bio-absorbable cross-linked gel of the present invention provides an excellent absorbable cellular interface suitable for use with a surgical instrument or implantable medical device.

It should be noted that as utilized herein, the non-polymeric bio-absorbable cross-linked gel of the invention can be derived from an oil such as fish oil, as well as fish oil fatty acid. As used herein, fish oil fatty acid includes, but is not limited to, omega-3 fatty acid, fish oil fatty acid, free fatty acid, monoglycerides, di-glycerides, or triglycerides, esters of fatty acids, or a combination thereof. The fish oil fatty acid includes one or more of arachidic acid, gadoleic acid, arachidonic acid, eicosapentaenoic acid, docosahexaenoic acid or derivatives, analogs and pharmaceutically acceptable salts thereof. Furthermore, as utilized herein, the term free fatty acid includes but is not limited to one or more of butyric acid, caproic acid, caprylic acid, capric acid, lauric acid, myristic acid, palmitic acid, palmitoleic acid, stearic acid, oleic acid, vaccenic acid, linoleic acid, alpha-linolenic acid, gamma-linolenic acid, behenic acid, erucic acid, lignoceric acid, analogs and pharmaceutically acceptable salts thereof. The biocompatible oils, including fish oil, are cured as described herein to form a hydrophobic cross-linked gel.

Likewise, it should be noted that to the extent utilized herein to describe the present invention, the term "vitamin E" and the term "alpha and gamma-tocopherols", are intended to refer to the same or substantially similar substance, such that they are interchangeable and the use of one includes an implicit reference to both. Further included in association with the term vitamin E are such variations including but not limited to one or more of alpha and gamma-tocopherols, beta-tocopherol, delta-tocopherol, gamma-tocopherol, alpha-tocotrienol, beta-tocotrienol, delta-tocotrienol, gamma-tocotrienol, alpha and gamma-tocopherols acetate, beta-tocopherol acetate, gamma-tocopherol acetate, delta-tocopherol acetate, alpha-tocotrienol acetate, beta-tocotrienol acetate, delta-tocotrienol acetate, gamma-tocotrienol acetate, alpha and gamma-tocopherols succinate, beta-tocopherol succinate, gamma-tocopherol succinate, delta-tocopherol succinate, alpha-tocotrienol succinate, beta-tocotrienol succinate, delta-tocotrienol succinate, gamma-tocotrienol succinate, mixed tocopherols, vitamin E TPGS, derivatives, analogs and pharmaceutically acceptable salts thereof.

With regard to the aforementioned oils, it is generally known that the greater the degree of unsaturation in the fatty acids the lower the melting point of a fat, and the longer the hydrocarbon chain the higher the melting point of the fat. A polyunsaturated fat, thus, has a lower melting point, and a saturated fat has a higher melting point. Those fats having a lower melting point are more often oils at room temperature. Those fats having a higher melting point are more often waxes or solids at room temperature. Therefore, a fat having the physical state of a liquid at room temperature is an oil. In general, polyunsaturated fats are liquid oils at room temperature, and saturated fats are waxes or solids at room temperature.

Polyunsaturated fats are one of four basic types of fat derived by the body from food. The other fats include saturated fat, as well as monounsaturated fat and cholesterol. Polyunsaturated fats can be further composed of omega-3 fatty acids and omega-6 fatty acids. Under the convention of naming the unsaturated fatty acid according to the position of its first double bond of carbons, those fatty acids having their first double bond at the third carbon atom from the methyl end of the molecule are referred to as omega-3 fatty acids. Likewise, a first double bond at the sixth carbon atom is called an omega-6 fatty acid. There can be both monounsaturated and polyunsaturated omega fatty acids.

Omega-3 and omega-6 fatty acids are also known as essential fatty acids because they are important for maintaining good health, despite the fact that the human body cannot make them on its own. As such, omega-3 and omega-6 fatty acids must be obtained from external sources, such as food. Omega-3 fatty acids can be further characterized as containing eicosapentaenoic acid (EPA), docosahexanoic acid (DHA), and alpha-linolenic acid (ALA). Both EPA and DHA are known to have anti-inflammatory effects and wound healing effects within the human body.

Oil that is hydrogenated becomes a waxy solid. Attempts have been made to convert the polyunsaturated oils into a wax or solid to allow the oil to adhere to a device for a longer period of time. One such approach is known as hydrogenation, which is a chemical reaction that adds hydrogen atoms to an unsaturated fat (oil) thus saturating it and making it solid at room temperature. This reaction requires a catalyst, such as a heavy metal, and high pressure. The resultant material forms a non-cross linked semi-solid. Hydrogenation can reduce or eliminate omega-3 fatty acids and any therapeutic effects (both anti-inflammatory and wound healing) they offer.

For long term controlled release applications, synthetic polymers, as previously mentioned, have been utilized in combination with a therapeutic agent. Such a combination provides a platform for the controlled long term release of the therapeutic agent from a medical device. However, synthetic polymer coatings have been determined to cause inflammation in body tissue. Therefore, the polymer coatings often must include at least one therapeutic agent that has an anti-inflammatory effect to counter the inflammation caused by the polymer delivery agent. In addition, patients that receive a synthetic polymer coating based implant must also follow a course of systemic anti-inflammatory therapy, to offset the inflammatory properties of the non-absorbable polymer. Typical anti-inflammatory agents are immunosuppressants and systemic delivery of anti-inflammatory agents can sometimes lead to additional medical complications, such as infection or sepsis, which can lead to long term hospitalization or death. Use of the non-polymeric bio-absorbable cross-linked gel described herein can negate the necessity of anti-inflammatory therapy, and the corresponding related risks described, because there is no inflammatory reaction to the non-polymeric bio-absorbable cross-linked gel.

FIGS. 1 through 13, wherein like parts are designated by like reference numerals throughout, illustrate an example embodiment of a coated biocompatible mesh structure that includes a biocompatible mesh structure and a coating derived from a biocompatible oil and can additionally include vitamin E according to the present invention. Although the present invention will be described with reference to the example embodiments illustrated in the figures, it should be understood that many alternative forms can embody the present invention. One of ordinary skill in the art will additionally appreciate different ways to alter the parameters of the embodiments disclosed, such as the size, shape, or type of elements or materials, in a manner still in keeping with the spirit and scope of the present invention.

FIG. 1 illustrates a coated surgical mesh, represented as a biocompatible mesh structure 10, in accordance with one embodiment of the present invention. The biocompatible mesh structure 10 is flexible, to the extent that it can be placed in a flat, curved, or rolled, configuration within a patient. The biocompatible mesh structure 10 is implantable, for both short term and long term applications. Depending on the particular formulation of the biocompatible mesh structure 10, the biocompatible mesh structure 10 will be present after implantation for a period of hours to days, or possibly months, or permanently.

The biocompatible mesh structure 10 is coated with a coating 20 derived from a biocompatible oil and may further include vitamin E. One example embodiment of the present invention makes use of fish oil as the biocompatible oil in part because of the high content of omega-3 fatty acids, which provide healing support for damaged tissue, as discussed above. The fish oil also serves as an anti-adhesion agent. In addition, the fish oil maintains anti-inflammatory or non-inflammatory properties as well. Vitamin E also maintains anti-inflammatory or non-inflammatory properties and further provides an anti-oxidant effect, as described above. The present invention is not limited to formation of the coating 20 with fish oil. Other suitable oils may be used in the coating 20, for example, vegetable or seed oils. However, the following description makes reference to the use of fish oil as one example embodiment.

Referring again to FIG. 1, it should be noted that the biocompatible mesh structure 10 is composed of a plurality of inter-coupled strands 30 forming a plurality of interstices 40 therebetween. The coating 20 derived from a biocompatible oil an potentially also vitamin E encapsulates the plurality of inter-coupled strands 30 while maintaining the spaces of the plurality of interstices 40.

One aspect of the biocompatible mesh structure 10 mentioned herein is that it has anti-adhesion characteristics or properties. By anti-adhesion, what is meant is a characteristic whereby the incidence, extent, and severity of postoperative adhesions, or other lacerations or tissue injuries, between different tissues and organs is reduced. The anti-adhesion characteristic results from the materials used to form the coating 20.

More specifically, the coating 20 provides a lubricious and/or anti-adhesive surface against tissue. The coating 20 can provide physical anti-adhesion functionality between two sections of tissue, or the coating 20 can form an anti-adhesion surface on a medical device, such as the biocompatible mesh structure 10. The use of the biocompatible oil provides extra lubrication to the surface of the medical device, which helps to reduce injury. With less injury, there is less of an inflammatory response, and less healing required. Vitamin E likewise provides anti-inflammatory and anti-oxidant properties, thus reducing the occurrence of inflammatory response and also adhesions due to inflammation. The oily surface of the coating 20 provides the anti-adhesion characteristics. One of ordinary skill in the art will appreciate that different oils will have different anti-adhesive properties, and the oils can be modified to be more liquefied or more solid or waxy, as desired. Accordingly, the degree of anti-adhesive properties offered by the coating 20 can vary.

Another aspect of the present invention is that the coating 20 is formed of the bio-absorbable material, such as naturally occurring fish oil, in accordance with the example embodiment described herein. The bio-absorbable properties of the naturally occurring oil enable the coating 20 to be absorbed by the cells of the body tissue (i.e., bio-absorbable). In example embodiments of the present invention, the bio-absorbable coating 20 contains lipids, many of which originate as triglycerides. It has previously been demonstrated that triglyceride byproducts, such as partially hydrolyzed triglycerides and fatty acid molecules can integrate into cellular membranes and enhance the solubility of drugs into the cell. Whole triglycerides are known not to enhance cellular uptake as well as partially hydrolyzed triglyceride, because it is difficult for whole triglycerides to cross cell membranes due to their relatively larger molecular size. Vitamin E compounds can also integrate into cellular membranes resulting in decreased membrane fluidity and cellular uptake.

Compounds that move too rapidly through a tissue may not be effective in providing a sufficiently concentrated dose in a region of interest. Conversely, compounds that do not migrate in a tissue may never reach the region of interest. Cellular uptake enhancers such as fatty acids and cellular uptake inhibitors such as alpha-tocopherol can be used alone or in combination to provide an effective transport of a given compound to a given region or location. Both fatty acids and alpha-tocopherol are accommodated by the coating 20 of the present invention described herein. Accordingly, fatty acids and alpha-tocopherol can be combined in differing amounts and ratios to contribute to a coating 20 in a manner that provides control over the cellular uptake characteristics of the coating 20 and any therapeutic agents mixed therein.

For example, the amount of alpha-tocopherol can be varied in the coating 20. Alpha-tocopherol is known to slow autoxidation in fish oil by reducing hydroperoxide formation. In addition alpha-tocopherol can be used to increase solubility of drugs in the fish oil forming the coating 20. Thus, varying the amount of alpha-tocopherol present in the coating 20 can impact the resulting formation. Alpha-tocopherol can actually protect the therapeutic drug during curing, which increases the resulting drug load in the coating 20 after curing. Furthermore, with certain therapeutic drugs, the increase of alpha-tocopherol in the coating 20 serves to slow and extend drug release due to the increased solubility of the drug in the alpha-tocopherol component of the coating 20. This reflects the cellular uptake inhibitor functionality of alpha-tocopherol, in that the uptake of the drug is slowed and extended over time.

The ratio of the fish oil to the vitamin E is not particularly limited. For example, the ratio of the fish oil to the vitamin E by weight may be about 0:100, about 5:95, about 10:90, about 15:85, about 20:80, about 25:75, about 30:70, about 35:65, about 40:60, about 45:55, about 50:50, about 55:45, about 60:40, about 65:35, about 70:30, about 75:25, about 80:20, about 85:15, about 90:10, about 95:5 or about 100:0. The term "about," as used with reference to the ratio of fish oil to vitamin E refers to ±5.0% by weight. In one embodiment, the ratio of fish oil to vitamin E is 100:0. In another embodiment, the ratio of fish oil to the vitamin E is 80:20. The ratio of the fish oil to the vitamin E may be modified in order to provide for controlled release or to increase the solubility of a therapeutic agent.

It should further be emphasized that the bio-absorbable nature of the coating 20 results in the coating 20 being completely absorbed over time by the cells of the body tissue. There are no substances in the coating 20, or break down products of the coating 20, that induce an inflammatory response. The coating 20 is generally composed of, or derived from, omega-3 fatty acids bound to triglycerides, potentially also including a mixture of free fatty acids and vitamin E (alpha-tocopherol). The triglycerides are broken down by lipases (enzymes) which result in free fatty acids that can than be transported across cell membranes. Subsequently, fatty acid metabolism by the cell occurs to metabolize any substances originating with the coating 20. The bio-absorbable nature of the coating 20 of the present invention results in the coating 20 being absorbed over time, leaving only an underlying delivery or other medical device structure that is biocompatible. There is no substantive foreign body inflammatory response to the bio-absorbable coating 20.

Although the coating 20 of the present invention is bio-absorbable to the extent that the coating 20 experiences the uptake into or through body tissues, in the specific embodiment described herein formed using naturally occurring oils, the exemplar oils are also lipid based oils. The lipid content of the oils provides a highly bio-absorbable coating 20. More specifically, there is a phospholipids layer in each cell of the body tissue. The fish oil, and equivalent oils, contains lipids as well. There is a lipophilic action that results where the lipids are attracted by each other in an effort to escape the aqueous environment surrounding the lipids.

A further aspect of the coating 20 is that the specific type of oil can be varied, and can contain elements beneficial to healing. The biocompatible mesh structure 10 coated with coating 20 also provides a natural scaffold for cellular growth and remodeling with clinical applications in general surgery, spinal repair, orthopedic surgeries, tendon and ligament repairs, gynecological and pelvic surgeries, and nerve repair applications. The addition of therapeutic agents to the coatings used in these applications can be utilized for additional beneficial effects, such as pain relief or infection minimization. In addition, non-surgical applications include external wound care, such as a treatment for burns or skin ulcers, without therapeutics as a clean, non-permeable, non-adhesive, anti-inflammatory, non-inflammatory dressing, or with added therapeutics for additional beneficial effects.

Another aspect of the biocompatible mesh structure 10 mentioned above is that the coating 20 thereon can contain therapeutic agents for delivery to the body tissue. Therapeutic agents have been delivered to a targeted location in a human utilizing a number of different methods in the past. For example, agents may be delivered nasally, transdermally, intravenously, orally, or via other conventional methods. Delivery may vary by release rate (i.e., quick release or slow release). Delivery may also vary as to how the drug is administered. Specifically, a drug may be administered locally to a targeted area, or administered systemically.

As utilized herein, the phrase "therapeutic agent(s)" refers to a number of different drugs or agents available, as well as future agents that may be beneficial for use with the coating 20 of the present invention. Therapeutic agents can be added to the coating 20, and/or the medical device in combination with the coating 20 as discussed herein. The therapeutic agent can take a number of different forms including anti-oxidants, anti-inflammatory agents, anti-coagulant agents, drugs to alter lipid metabolism, anti-proliferatives, anti-neoplastics, tissue growth stimulants, functional protein/factor delivery agents, anti-infective agents, anti-imaging agents, anesthetic agents, therapeutic agents, tissue absorption enhancers, anti-adhesion agents, germicides, anti-septics, analgesics, pro-drugs, and any additional desired therapeutic agents such as those listed in Table 5 below.

TABLE #1

| CLASS | EXAMPLES |
| --- | --- |
| Antioxidants | Alpha-tocopherol, lazaroid, probucol, phenolic antioxidant, resveretrol, AGI-1067, vitamin E |
| Antihypertensive Agents | Diltiazem, nifedipine, verapamil |
| Antiinflammatory Agents | Glucocorticoids (e.g. dexamethazone, methylprednisolone), leflunomide, NSAIDS, ibuprofen, acetaminophen, hydrocortizone acetate, hydrocortizone sodium phosphate, macrophage-targeted bisphosphonates |
| Growth Factor Antagonists | Angiopeptin, trapidil, suramin |
| Antiplatelet Agents | Aspirin, dipyridamole, ticlopidine, clopidogrel, GP IIb/IIIa inhibitors, abcximab |
| Anticoagulant Agents | Bivalirudin, heparin (low molecular weight and unfractionated), wafarin, hirudin, enoxaparin, citrate |
| Thrombolytic Agents | Alteplase, reteplase, streptase, urokinase, TPA, citrate |
| Drugs to Alter Lipid Metabolism (e.g. statins) | Fluvastatin, colestipol, lovastatin, atorvastatin, amlopidine |
| ACE Inhibitors | Elanapril, fosinopril, cilazapril |
| Antihypertensive Agents | Prazosin, doxazosin |
| Antiproliferatives and Antineoplastics | Cyclosporine, cochicine, mitomycin C, sirolimus micophenonolic acid, rapamycin, everolimus, tacrolimus, paclitaxel, QP-2, actinomycin, estradiols, dexamethasone, methatrexate, cilostazol, prednisone, cyclosporine, doxorubicin, ranpirnas, troglitzon, valsarten, pemirolast, C-MYC antisense, angiopeptin, vincristine, PCNA ribozyme, 2-chloro-deoxyadenosine |
| Tissue growth stimulants | Bone morphogeneic protein, fibroblast growth factor |
| Promotion of hollow organ occlusion or thrombosis | Alcohol, surgical sealant polymers, polyvinyl particles, 2-octyl cyanoacrylate, hydrogels, collagen, liposomes |
| Functional Protein/Factor delivery | Insulin, human growth hormone, estradiols, nitric oxide, endothelial progenitor cell antibodies |
| Second messenger targeting | Protein kinase inhibitors |
| Angiogenic | Angiopoetin, VEGF |
| Anti-Angiogenic | Endostatin |
| Inhibition of Protein Synthesis/ECM formation | Halofuginone, prolyl hydroxylase inhibitors, C-proteinase inhibitors |
| Antiinfective Agents | Penicillin, gentamycin, adriamycin, cefazolin, amikacin, ceftazidime, tobramycin, levofloxacin, silver, copper, hydroxyapatite, vancomycin, ciprofloxacin, rifampin, mupirocin, RIP, kanamycin, brominated furonone, algae |

TABLE #1-continued

| CLASS | EXAMPLES |
|---|---|
|  | byproducts, bacitracin, oxacillin, nafcillin, floxacillin, clindamycin, cephradin, neomycin, methicillin, oxytetracycline hydrochloride, Selenium. |
| Gene Delivery | Genes for nitric oxide synthase, human growth hormone, antisense oligonucleotides |
| Local Tissue perfusion | Alcohol, $H_2O$, saline, fish oils, vegetable oils, liposomes |
| Nitric oxide Donor Derivatives | NCX 4016 - nitric oxide donor derivative of aspirin, SNAP |
| Gases | Nitric oxide, compound solutions |
| Imaging Agents | Halogenated xanthenes, diatrizoate meglumine, diatrizoate sodium |
| Anesthetic Agents | Lidocaine, benzocaine |
| Descaling Agents | Nitric acid, acetic acid, hypochlorite |
| Anti-Fibrotic Agents | Interferon gamma-1b, Interluekin-10 |
| Immunosuppressive/Immunomodulatory Agents | Cyclosporine, rapamycin, mycophenolate motefil, leflunomide, tacrolimus, tranilast, interferon gamma-1b, mizoribine |
| Chemotherapeutic Agents | Doxorubicin, paclitaxel, tacrolimus, sirolimus, fludarabine, ranpirnase |
| Tissue Absorption Enhancers | Fish oil, squid oil, omega 3 fatty acids, vegetable oils, lipophilic and hydrophilic solutions suitable for enhancing medication tissue absorption, distribution and permeation |
| Anti-Adhesion Agents | Hyaluronic acid, human plasma derived surgical sealants, and agents comprised of hyaluronate and carboxymethylcellulose that are combined with dimethylaminopropyl, ehtylcarbodimide, hydrochloride, PLA, PLGA |
| Ribonucleases | Ranpirnase |
| Germicides | Betadine, iodine, sliver nitrate, furan derivatives, nitrofurazone, benzalkonium chloride, benzoic acid, salicylic acid, hypochlorites, peroxides, thiosulfates, salicylanilide |
| Antiseptics | Selenium |
| Analgesics | Bupivicaine, naproxen, ibuprofen, acetylsalicylic acid |

Some specific examples of therapeutic agents useful in the anti-restenosis realm include cerivastatin, cilostazol, fluvastatin, lovastatin, paclitaxel, pravastatin, rapamycin, a rapamycin carbohydrate derivative (for example, as described in US Patent Application Publication 2004/0235762), a rapamycin derivative (for example, as described in U.S. Pat. No. 6,200,985), everolimus, seco-rapamycin, seco-everolimus, and simvastatin. With systemic administration, the therapeutic agent is administered orally or intravenously to be systemically processed by the patient. However, there are drawbacks to a systemic delivery of a therapeutic agent, one of which is that the therapeutic agent travels to all portions of the patient's body and can have undesired effects at areas not targeted for treatment by the therapeutic agent. Furthermore, large doses of the therapeutic agent only amplify the undesired effects at non-target areas. As a result, the amount of therapeutic agent that results in application to a specific targeted location in a patient may have to be reduced when administered systemically to reduce complications from toxicity resulting from a higher dosage of the therapeutic agent.

Accordingly, an alternative to the systemic administration of a therapeutic agent is the use of a targeted local therapeutic agent delivery approach. With local delivery of a therapeutic agent, the therapeutic agent is administered using a medical device or apparatus, directly by hand, or sprayed on the tissue, at a selected targeted tissue location of the patient that requires treatment. The therapeutic agent emits, or is otherwise delivered, from the medical device apparatus, and/or carrier, and is applied to the targeted tissue location. The local delivery of a therapeutic agent enables a more concentrated and higher quantity of therapeutic agent to be delivered directly at the targeted tissue location, without having broader systemic side effects. With local delivery, the therapeutic agent that escapes the targeted tissue location dilutes as it travels to the remainder of the patient's body, substantially reducing or eliminating systemic side effects.

Targeted local therapeutic agent delivery using a medical device can be further broken into two categories, namely, short term and long term ranging generally within a matter of seconds or minutes to a few days or weeks to a number of months. Typically, to achieve the long term delivery of a therapeutic agent, the therapeutic agent must be combined with a delivery agent, or otherwise formed with a physical impediment as a part of the medical device, to slow the release of the therapeutic agent.

Prior attempts to create films and drug delivery platforms, such as in the field of stents, primarily make use of high molecular weight synthetic polymer based materials to provide the ability to better control the release of the therapeutic agent. Essentially, the polymer in the platform releases the drug or agent at a predetermined rate once implanted at a location within the patient. Regardless of how much of the therapeutic agent would be most beneficial to the damaged tissue, the polymer releases the therapeutic agent based on properties of the polymer. Accordingly, the effect of the therapeutic agent is substantially local at the surface of the tissue making contact with the medical device having the coating. In some instances the effect of the therapeutic agent is further localized to the specific locations of, for example, stent struts or mesh pressed against the tissue location being treated. These prior approaches can create the potential for a localized toxic effect.

The coating 20 of the present invention, however, makes use of the natural oils to form a non-polymeric natural oil based therapeutic agent delivery platform, if desired. Furthermore, the coating 20 can be formed in a manner that creates the potential for controlled long term release of a therapeutic agent, while still maintaining the benefits of the natural oil component of the coating 20.

More specifically, it is known that oil that is oxygenated becomes a waxy solid. Attempts have been made to convert the polyunsaturated oils into a wax or solid to allow the oil to adhere to a device for a longer period of time. One such approach applies the oil to the medical device and allows the oil to dry.

With the present invention, and in the field of soft tissue applications, and in part because of the lipophilic mechanism enabled by the bio-absorbable lipid based coating 20 of the present invention, the uptake of the therapeutic agent is facilitated by the delivery of the therapeutic agent to the cell membrane by the bio-absorbable coating 20. Further, the therapeutic agent is not freely released into the body fluids, but rather, is delivered directly to the cells and tissue. In prior configurations using polymer based coatings, the drugs were released at a rate regardless of the reaction or need for the drug on the part of the cells receiving the drug.

In addition, when the oil provided to form the coating 20 is a naturally occurring oil containing the omega-3 fatty acids (including DHA and EPA), the process for forming the coating 20 can be tailored to avoid causing detrimental effects to the beneficial properties of the omega-3 fatty acids, or at least effects too detrimental to have any lasting effect. As described herein, certain properties of the fatty acids may lose their effectiveness, however other desired properties are maintained. If there is no concern for maintaining the beneficial effects, the curing and other steps leading to the formation of the coating 20 can include steps that may reduce some of the beneficial properties of the omega-3 fatty acids, as understood by one of ordinary skill in the art. Example embodiments illustrating the formation and different configurations of the coating 20 are provided herein.

The coating 20 of the present invention serves, in part, to shield the tissue from the underlying biocompatible mesh structure 10 at the time of implantation to lessen or eliminate the inflammatory and foreign body responses. In accordance with the example embodiments described herein, the coating 20 is derived from fish oil and can further include vitamin E, where the fish oil can be derived from fatty acid compounds (I.e., omega-3 fatty acids). In one aspect of the present invention, the coating 20 is cured, for example, by heat, UV light, chemical means, reaction with biologically active agent and/or reactive gasses. In one example embodiment, the coating 20 is cured by heating the fish oil. As liquid fish oil is heated, autoxidation occurs with the absorption of oxygen into the fish oil to create hydroperoxides in an amount dependent upon the amount of unsaturated (C═C) sites in the fish oil. However, the (C═C) bonds are not consumed in the initial reaction. Concurrent with the formation of hydroperoxides is the isomerization of (C═C) double bonds from cis to trans in addition to double bond conjugation. It has been demonstrated that hydroperoxide formation increases with temperature. Heating of the fish oil allows for cross-linking between the fish oil unsaturated chains using a combination of peroxide (C—O—O—C), ether (C—O—C), and hydrocarbon (C—C) bridges. The formation of the cross-links results in gelation of the fish oil after the (C═C) bonds have substantially isomerized into the trans configuration. The (C═C) bonds can also form C—C cross-linking bridges in the glyceride hydrocarbon chains using a Diels-Alder Reaction. In addition to solidifying the coating 20 through cross-linking, both the hydroperoxide and (C═C) bonds can undergo secondary reactions converting them into lower molecular weight secondary oxidation byproducts including aldehydes, ketones, alcohols, fatty acids, esters, lactones, ethers, and hydrocarbons.

FIG. 2 is a flow chart illustrating one example method of preparing the coated mesh structure. Accordingly, a biocompatible mesh structure 10 is provided (step 200). In one embodiment, the mesh is constructed of a biocompatible knitted polypropylene monofilament composed of a plurality of inter-coupled strands 30 forming a plurality of interstices 40 therebetween. The mesh structure may be untreated or pre-treated, for example, by plasma etching. It is advantageous in some embodiments to treat the mesh structure prior to coating in order to improve the adhesive forces between the coating 20 and the mesh, and to diminish coating flow and pooling and to provide a more continuous coating 20.

Upon providing the mesh structure, the coating 20 is prepared (step 210). The coating 20 of the invention is derived from a biocompatible oil and may further include vitamin E. The coating 20 may be prepared by mixing, for example, fish oil, vitamin E, or a combination thereof, and optionally a therapeutic agent, together by any suitable mixing techniques include, for example, vortexing, sonicating, stirring, rolling, or shaking, or other methods of mixing well known in the art.

In one particular embodiment, the coating 20 for the biocompatible mesh structure 10 may comprise one or more therapeutic agents. The amount of the one or more therapeutic agents may comprise at least about 0.5-50% by weight of the coating 20. The term "about," as used with reference to the percentage by weight of therapeutic agent refers to ±0.5% by weight of the therapeutic agent compared to the coating 20. In one example embodiment, the coating 20 may comprise may comprise at least between about 6-7% by weight of one or more therapeutic agents.

The amount of the therapeutic agent in the present invention, in one embodiment, can be an effective amount. The term "effective amount" as used herein, refers to that amount of a compound sufficient to result in amelioration of symptoms, e.g., treatment, healing, prevention or amelioration of the relevant medical condition, or an increase in rate of treatment, healing, prevention or amelioration of such conditions. When applied to an individual active ingredient, administered alone, an effective amount refers to that ingredient alone. When applied to a combination, an effective amount can refer to combined amounts of the active ingredients that result in the therapeutic effect, whether administered in combination, serially or simultaneously. In various embodiments, where formulations comprise two or more therapeutic agents, such formulations can be described as an effective amount of compound A for indication A and an effective amount of compound B for indication B, such descriptions refer to amounts of A that have a therapeutic effect for indication A, but not necessarily indication B, and amounts of B that have a therapeutic effect for indication B, but not necessarily indication A. In a further embodiment, one of the therapeutic agents may have a synergistic effect on another therapeutic agent in a combination of therapeutic agents. Moreover, each therapeutic agent may have a synergistic effect on any other therapeutic agent provided in the invention. As used herein, "synergy" or "synergistic effect" refers to an enhancement of the therapeutic properties of one or more therapeutic agents of the invention. Furthermore two or more compounds may be administered for the same or different indication with or without a true synergism. In another embodiment, compound A can have an enhancement effect on compound B and compound B can have an enhancement effect on compound A. In another embodiment, A and B may have no effect upon each other.

The type of therapeutic agent for use with the coated mesh structure is not particularly limited. In one embodiment, the therapeutic agent is an agent listed in Table 1, or analogues, derivatives and prodrugs thereof. The term "derivative," as used herein, refers to a therapeutic agent derived or obtained from a known therapeutic agent and contains the essential elements of the therapeutic agent. The term "analog," as used herein, refers to a therapeutic agent with a similar structure to that of a known therapeutic agent, but differs slightly in composition. Further, a "prodrug" refers to an inactive precursor of a known therapeutic agent which is converted into the active form of SAR-943, TAFA-93 or rapamycin in the body by normal metabolic processes. In another embodiment, the therapeutic agent is an agent which provides similar therapeutic effects ananti-proliferative drug.

The therapeutic agent may be mixed with the coating 20 by any suitable mixing techniques known in the art. In one embodiment, the therapeutic agent may be dissolved or suspended in the fish oil alone, then mixed with the vitamin E, or may be dissolved or suspended in the vitamin E, then mixed with the fish oil. Alternatively, the therapeutic agent may be dissolved or suspended in the combined vitamin E and fish oil. In another embodiment, the therapeutic agent can be first dissolved or suspended in a solvent, and subsequently mixed with the fish oil, the vitamin E or a combination thereof and the solvent may then be removed. The solvent can be selected based on the identified therapeutic agent. One skilled in the art will be able to determine the appropriate solvent to use. The solvent can be a solvent or mixture of solvents and include solvents that are generally acceptable for pharmaceutical use. Suitable solvents include, for example: alcohols and polyols, such as $C_2$-$C_6$ alkanols, 2-ethoxyethanol, ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, and polypropylene glycol; amides, such as 2-pyrrolidone, 2-piperidone, 2-caprolactam, N-alkylpyrrolidone, N-methyl-2-pyrrolidone, N-hydroxyalkylpyrrolidone, N-alkylpiperidone, N-alkylcaprolactam, dimethylacetamide; esters, such as ethyl acetate, methyl acetate, butyl acetate, ethylene glycol diethyl ether, ethylene glycol dimethyl ether, propylene glycol dimethyl ether, ethyl proprionate, tributylcitrate, acetyl triethylcitrate, acetyl tributyl citrate, triethylcitrate, ethyl oleate, ethyl caprylate, ethyl cutyrate, tracetin, $\epsilon$-caprolactone and isomers thereof, $\delta$-valerolactorne and isomers thereof, $\beta$-butyrolactone and isomers thereof; and other solvents, such as water, dimethylsulfoxide, benzyl benzoate, ethyl lactate, acetone, methylethyl ketone, dimethylsolfone, tetrahydrofuran, decylmethylsufoxide, N,N-diethyl-m-toulamide or 1-dodecylazacycloheptan-2-one, hexane, chloroform, dichloromethane. Suitable solubility enhancers can include, for example, polyvinylalcohol, hydroxypropyl methylcellulose, and other celluloses, cyclodextrins and cyclodextrin derivatives.

The one or more therapeutic agents may also be added to the coating 20 derived from the oil and vitamin E by cryogrinding the one or more therapeutic agents into the coating 20. The term "cryogrinding" or "cryogenic grinding," as used herein, refers to grinding materials at very low temperatures, primarily using liquid nitrogen as the coolant. In another embodiment, the therapeutic agent may be dissolved or suspended in a solvent and the coated mesh structure may be subsequently coated with the solution containing the therapeutic agent (e.g., by dipping), followed by removal of the solvent. Alternatively, the therapeutic agent may be dissolved or suspended in a solvent and the uncoated mesh structure may be coated first with the solution containing the therapeutic agent, followed by removal of the solvent and coating of the mesh structure with the coating derived from the biocompatible oil and additionally vitamin E.

In one embodiment, the coating 20 for the biocompatible mesh structure 10 may be in at least a partially cured state prior to application of the coating 20 on the mesh. Curing generally refers to thickening, hardening, or drying of a material brought about by heat, UV light, chemical means, reaction with biologically active agent and/or reactive gasses. In another embodiment, the coating 20 is subjected to curing conditions subsequent to application of the coating 20 on the mesh, such that the coating 20 is resident on the mesh in at least a partially cured state.

The curing process can occur either prior to the addition of the therapeutic agent or after the addition of the therapeutic agent. Some curing methods have been indicated to have detrimental effects on the therapeutic agent combined with the omega-3 fatty acid, making them partially or completely ineffective. As such, oils, and more specifically oils containing omega-3 fatty acids, have been utilized as a delivery agent for the short term uncontrolled release of a therapeutic agent, so that minimal or no curing is required. However, there are no known uses of oils containing omega-3 fatty acids for combination with a therapeutic agent in a controlled release application that makes use of the therapeutic benefits of the omega-3 fatty acids. Further, some heating of the omega-3 fatty acids to cure the oil can lessen the total therapeutic effectiveness of the omega-3 fatty acids, but not eliminate the therapeutic effectiveness. One characteristic that can remain after certain curing by heating methods is the non-inflammatory response of the tissue when exposed to the cured omega-3 fatty acid material. As such, an oil containing omega-3 fatty acids can be heated for curing purposes, and still maintain some or even a majority of the therapeutic effectiveness of the omega-3 fatty acids. In addition, although the therapeutic agent combined with the omega-3 fatty acid and cured with the omega-3 fatty acid can be rendered partially ineffective, the portion remaining of the therapeutic agent can, in accordance with the present invention, maintain pharmacological activity and in some cases be more effective than an equivalent quantity of agent delivered with other coating materials.

Referring again to FIG. 2, upon preparation of the coating 20 derived from a biocompatible oil and potentially further including vitamin E, the mesh structure is then coated with the coating 20 (step 215). One of skill in the art will appreciate the methods available for coating the mesh structure. For example, the coating 20 may be sprayed, wiped or brushed onto the mesh structure. In one alternative, the mesh structure may be dipped into the prepared coating 20. In a particular embodiment, the coating 20 is applied to the mesh structure by single action, internal mix, siphon feed airbrush. One layer of the coating 20 may be applied to the biocompatible mesh structure 10. Alternatively, multiple layers of the coating 20 may be applied by any of the above-described methods. It is important to note that, depending on the method of applying the coating 20 to the mesh structure, the coating 20 may be chemically modified during the application process. In one embodiment, the coating 20 is dispersed on the biocompatible mesh structure 10 in an amount of between about 1.0 and 50.0 mg/in$^2$. In one example embodiment, the coating 20 is dispersed on the biocompatible mesh structure 10 in an amount of about 15.0 mg/in$^2$.

Subsequent to coating the mesh structure, the coated mesh structure is packaged (step 220) and sterilized (step 225). Packaging of the coated mesh structure can be effected by any method applicable. In one embodiment, the packaging of the coated mesh structure comprises a polyethylene terephthalate tray, a polyethylene terephthalate guard and a Tyvek® lid. Sterilization can be performed by a variety of different techniques that are well known in the art, including, for example, vaporized hydrogen peroxide, ethylene oxide (ETO) gas, radiation using gamma or electron-beam radiation, steam and gas plasma.

It should be noted that the present invention is not limited to the example embodiments illustrated. Rather the embodiments illustrated are merely example implementations of the present invention.

EXAMPLE #1

An 80:20 blend of fish oil to vitamin E was prepared by weight and mixed using a Vortex mixer. The oil blend was loaded into a single action, internal mix, siphon feed airbrush (Badger Airbrush Co., Model 200NH) fitted with the stock general purpose spray tip and needle. The airbrush was primed until the siphon feed is free of air bubbles. The spray volume was adjusted so that the oil blend was expressed at a rate of approximately 4 mg/s. For example:

The airbrush spray volume adjustment screw was opened 2.5 revolutions from fully closed. The oil blend was expressed at 25 psi into a container of known weight for 7 seconds. The container is reweighed resulting in a mass increase of 28.6 mg, which equated to a coating expression rate of 4.1 mg/s.

A piece of stock ProLite Ultra™ mesh was weighed and placed in a plastic tray. The edge of the mesh was held down against the plastic tray with forceps and the mesh was sprayed with the 80:20 fish oil to vitamin E blend for a predetermined length of time. While spraying, the airbrush was held approximately 6" away and was moved in a circular pattern around the edge of the mesh with some brief passes into the center. This process was repeated on the opposite side of the mesh. Because of the porosity of the mesh, some of the coating expressed during spraying passed through the mesh, adhered to the tray and was not considered when determining the amount of coating applied to the mesh. After spraying both sides, the mesh was removed from the tray, weighed again and the coating weight determined. The target coating weight per area of mesh was approximately 15 mg/in$^2$. It has been noted that coating concentrations greater than this resulted in increased transfer of the coating to surfaces other than the mesh. For example:

A 1"×1.4" (2.5 cm×3.5 cm) piece of stock ProLite Ultra mesh was weighed and the airbrush was adjusted to spray at a rate of 4 mg/s. The mesh was sprayed for 7 seconds on each side using the technique described above. The mesh was reweighed resulting is a mass increase of 21.3 mg, which equated to a coating concentration of 15.2 mg/in$^2$.

Also, a 2"×4" piece of stock ProLite Ultra mesh was weighed and the airbrush was adjusted to spray at a rate of 4 mg/s. The mesh was sprayed for approximately 40 seconds on each side using the technique described above. The mesh was reweighed resulting in a mass increase of 119.7 mg, which equated to a coating concentration of 15.0 mg/in$^2$.

Figure 3:
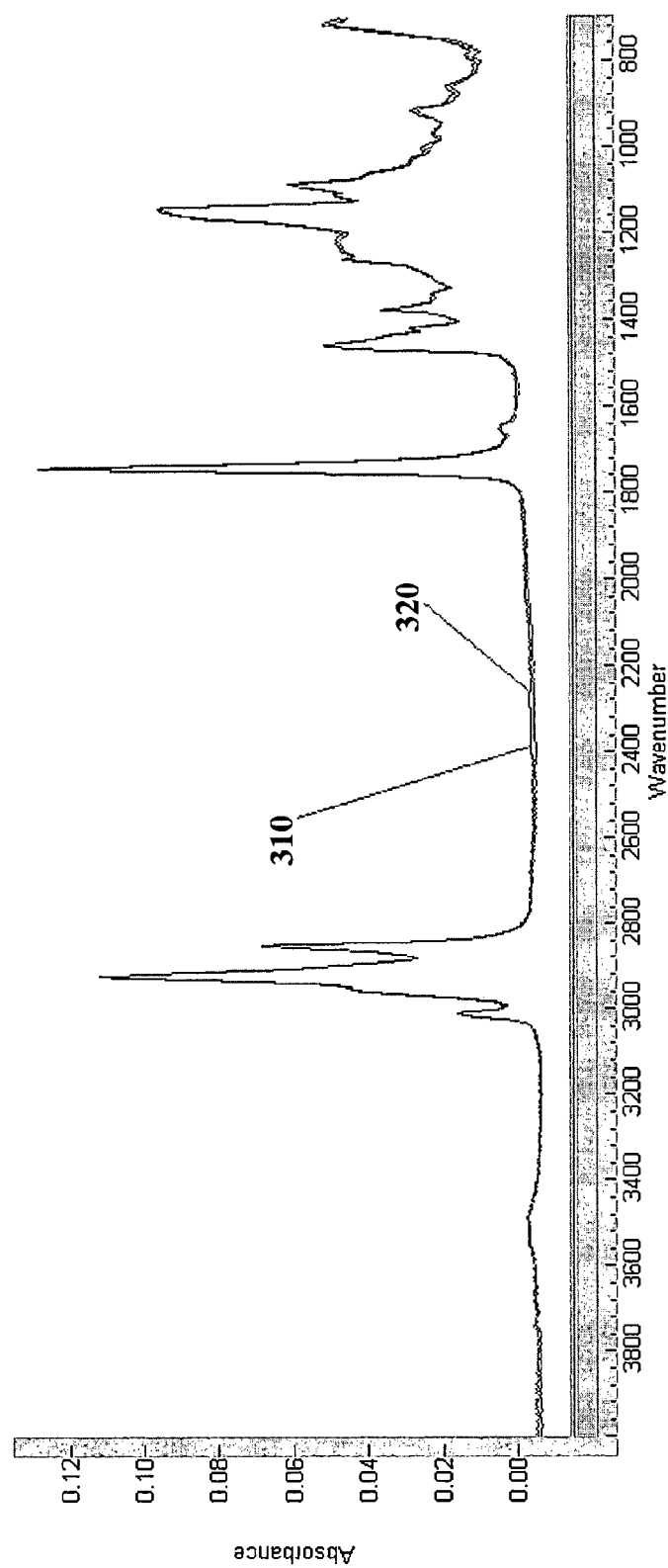
FIG. 3 is a Fourier Transform infrared (FTIR) spectra comparison of sprayed coating and non-sprayed coating, in accordance with another aspect of the present invention.

FTIR analysis of coating distribution using a Micro ATR fixture showed that the coating is present on all areas of the mesh, even in areas where the mesh is held down with forceps during spraying. FTIR analysis, as illustrated in FIG. 3, compared the coating derived from fish oil and vitamin E that was unsprayed (1010) with coating that had been sprayed with the single action, internal mix, siphon feed airbrush (Badger Airbrush Co., Model 200NH) fitted with the stock general purpose spray tip and needle (1020). This FTIR analysis indicated that spraying does not change the chemistry of the coating.

Figure 4:
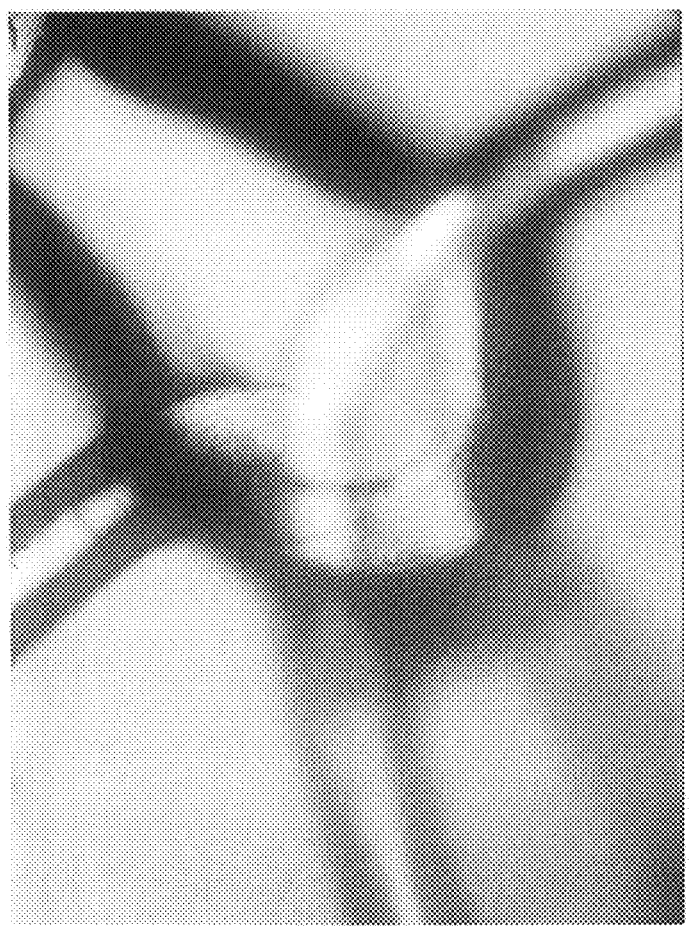
FIG. 4 is an optical microscopy image of a coated elevated loop of untreated monofilament of the coated mesh structure, in accordance with one embodiment of the present invention.
Figure 5:
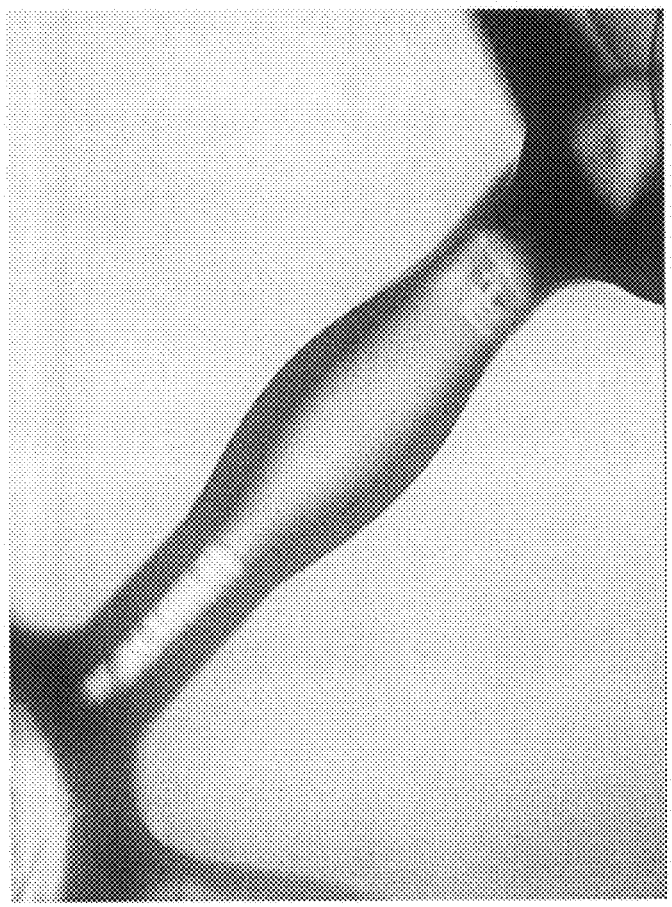
FIG. 5 is an optical microscopy image of a coated end of an untreated monofilament of the coated mesh structure, in accordance with one embodiment of the present invention.

FIGS. 4 and 5 provide optical microscopy images of coating distribution on the coated mesh structure. A more continuous coating was observed in the knits and in the middle of the monofilaments running between knits. Areas with a less continuous coating, such as the elevated loops of monofilaments within the knits (FIG. 4) and the ends of monofilaments running between the knits (FIG. 5) were analyzed using FTIR and coating was observed. Areas of more continuous coating can be explained by a weak adhesive force between the coating and the polypropylene, which allows the liquid coating to flow freely and pool.

Figure 6:
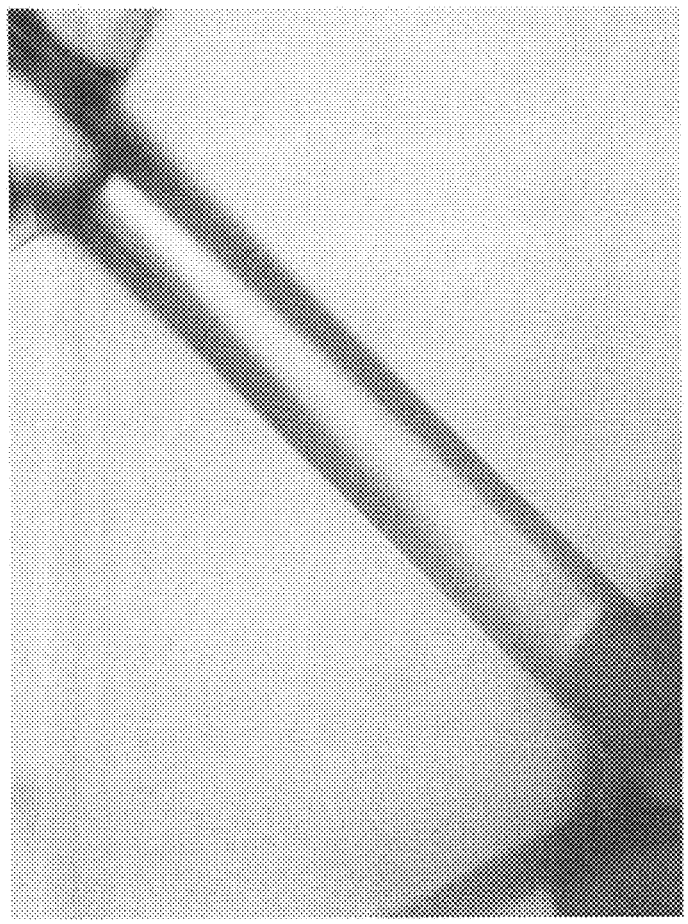
FIG. 6 is an optical microscopy image of a coated end of an oxygen plasma-etched monofilament of the coated mesh structure, in accordance with one embodiment of the present invention.

A more continuous coating on all areas of the mesh was achieved by treating the mesh surface prior to application of the coating. Surface treatments, such as plasma etching, improved the adhesive forces between the coating and the mesh, diminishing coating flow and pooling, which resulted in a more continuous coating. For example:

A 1"×1.4" (2.5 cm×3.5 cm) piece of stock ProLite Ultra mesh was placed in a plasma vacuum chamber and the air was removed until 50 mTorr of vacuum pressure was reached. Oxygen gas was introduced into the vacuum chamber until the vacuum pressure reached 250 mTorr. The mesh was exposed to an electrical current generated in the vacuum chamber for 5 minutes. Immediately after this plasma etching process, the mesh was weighed and spray coated using the process described above. The mesh was reweighed and coating distribution is assessed using optical microscopy. FIG. 6 is an optical microscopy image of coating distribution on the plasma-etched coated mesh structure, and illustrates that a more continuous coating was observed on the elevated loops of monofilaments within the knits and the ends of monofilaments running between the knits of oxygen plasma etched mesh when compared to untreated mesh.

EXAMPLE #2

The packaging used for sterilization and shipment can be designed to minimize transfer of the coating to the packaging materials. An example of a packaging configuration that demonstrates minimal coating transfer after sterilization is described below:

A 1"×1.4" piece of mesh was weighed and placed in the bottom of a polyethylene terephthalate (PETE) tray. A PETE guard was placed in the tray above the mesh and the package was sealed with a Tyvek lid. The guard prevents the mesh from coming in contact with the lid during subsequent handling. The packaged mesh was sterilized by vaporized hydrogen peroxide (VHP) using a 5.7 g injection cycle. After sterilization, the mesh was removed from the packaging and weighed. The change in mesh weight was equivalent to the amount of coating transferred to the packaging materials during packaging and sterilization. Table 2 provides data illustrating the reproducibility of the mesh coatings after coating, packaging and sterilization. The data shows that mesh packaged in this configuration exhibited an average of less than 2% coating transfer from the mesh during packaging and sterilization.

TABLE 2

| Sample # | Initial Mesh Weight (g) | Post-Spray Mesh Weight (g) | FO/VE Applied To Mesh (g) | Mesh weight after VHP and removal From Packaging (g) | FO/VE lost During Pack/VHP (g) | % FO/VE Lost to Pack/VHP |
|---|---|---|---|---|---|---|
| 1 | 0.0493 | 0.0709 | 0.0216 | 0.0708 | 0.0001 | 0.4630 |
| 2 | 0.0504 | 0.0712 | 0.0208 | 0.0697 | 0.0015 | 7.2115 |
| 3 | 0.0489 | 0.0704 | 0.0215 | 0.0704 | 0.0000 | 0.0000 |
| 4 | 0.0499 | 0.0723 | 0.0224 | 0.0723 | 0.0000 | 0.0000 |
| 5 | 0.0501 | 0.0723 | 0.0222 | 0.0722 | 0.0001 | 0.4505 |
| 6 | 0.0486 | 0.0688 | 0.0202 | 0.0688 | 0.0000 | 0.0000 |
| 7 | 0.0516 | 0.0729 | 0.0213 | 0.0716 | 0.0013 | 6.1033 |
| 8 | 0.0514 | 0.0740 | 0.0226 | 0.0739 | 0.0001 | 0.4425 |
| 9 | 0.0497 | 0.0705 | 0.0208 | 0.0700 | 0.0005 | 2.4038 |
| 10 | 0.0498 | 0.0695 | 0.0197 | 0.0694 | 0.0001 | 0.5076 |
| Ave | 0.0500 | 0.0713 | 0.0213 | 0.0709 | 0.0004 | 1.7582 |
| SD | 0.0010 | 0.0016 | 0.0009 | 0.0016 | 0.0006 | 2.6873 |

Figure 7:
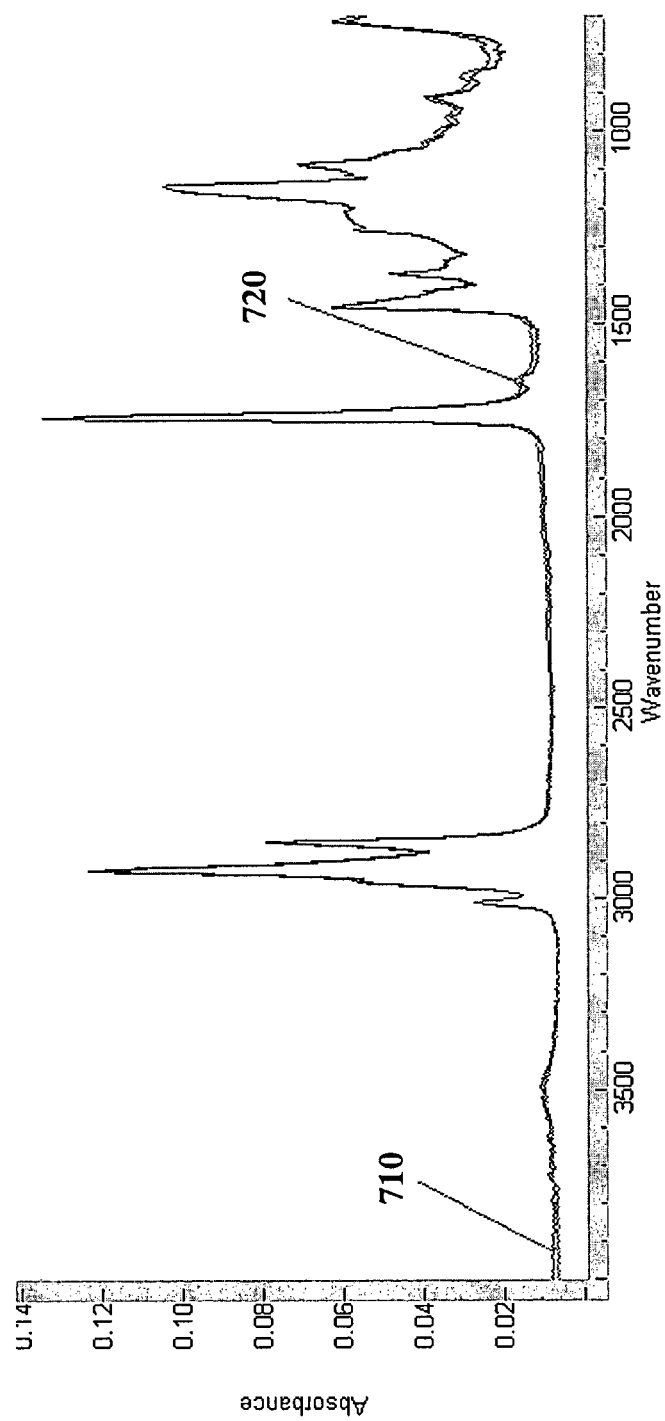
FIG. 7 is an FTIR spectra comparison of unsterilized coating and vaporized hydrogen peroxide sterilized (VHP) coating, in accordance with one embodiment of the present invention.

FIG. 7 is an FTIR analysis comparing the bulk coating (710) with the coated mesh structure after VHP sterilization (720). This FTIR analysis of the coating after VHP sterilization illustrates that the coating underwent no chemical during sterilization.

EXAMPLE #3

Drug Formulation and Release

Drug delivery experiments on α-Mesh were performed using several antiproliferative drugs in a fish oil/vitamin E formulation. All formulations were initially prepared to be about 15% drug in approximately 3 g of Ocean Nutrition fish oil, and were then cyroground in a Specs Sample Prep Cryogrinder to reduce drug particle size and thoroughly blend. A known amount of 80:20 fish oil to vitamin E coating was added to the cyroground formulation and mixed by vortexing, resulting in the final formulation used to spray the mesh. Drug percentages were calculated by obtaining weights at each step of the formulation procedure, with the final spray formulations containing about 6% drug. All samples were 1×1.4" Prolite Ultra mesh, and sprayed with the same technique as described above. For example, to achieve approximately 20 mg of coating on a piece of mesh, the airbrush sprayed a drug formulation at roughly 3.7 mg/s for 20 seconds (keeping in mind that not all of the coating sprayed in the 20 seconds is deposited onto the mesh).

Daily dissolutions were carried out in 0.01 M PBS solution at 37° C., and mesh extractions were performed in 30:70 0.5 M Acetic Acid/Acetonitrile diluent. All samples prepared for dissolution data were packaged in PETE trays with a PETE guard with a Tyvek lid, and VHP sterilized with a 5.7 g injection cycle. Percent recovery was determined by using the theoretical drug load as that obtained by coating weight, and actual drug load was calculated from drug detection through HPLC analysis. Extraction results for drug delivery on mesh are shown below in Table 3.

TABLE 3

| % Drug in spray formulation | Coating weight (mg) | Theoretical load (ug) | Actual load by HPLC (ug) | % Recovery | Sample Notes |
|---|---|---|---|---|---|
| 6.011 | 19.0 | 1142 | 1122 | 98.2 | N = 2 |
| 6.71 | 17.6 | 1181 | 1001 | 84.8 | N = 1 |
| 6.325 | 18.6 | 1176 | 927.6 | 78.9 | N = 1 |

Figure 8:
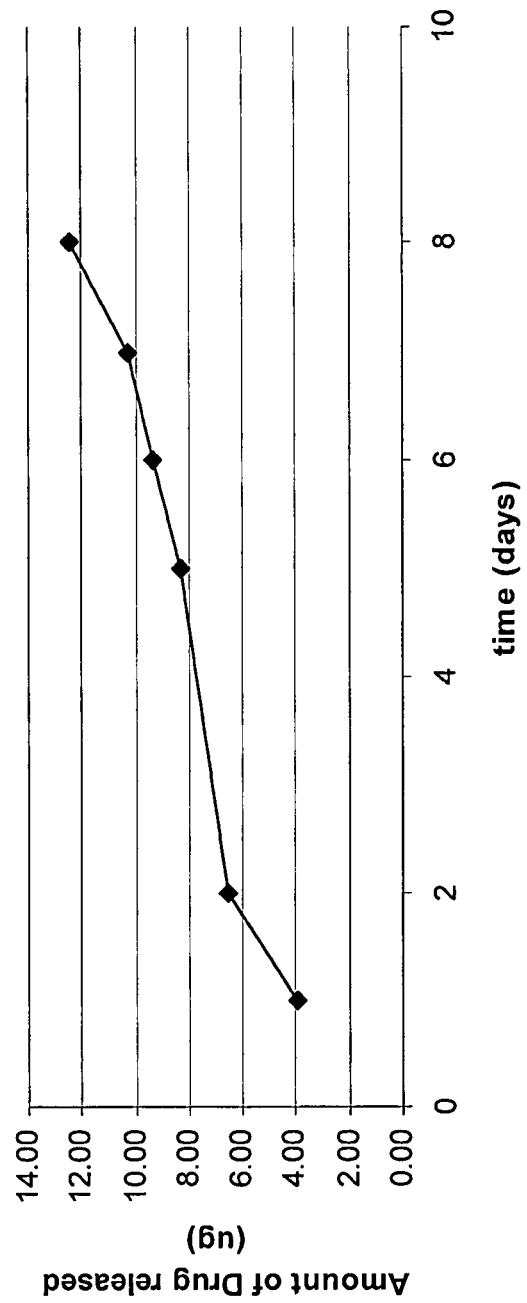
FIG. 8 is a chart illustrating the release of an anti-proliferative drug over time from the coated mesh structure, in accordance with one embodiment of the present invention.
Figure 9:
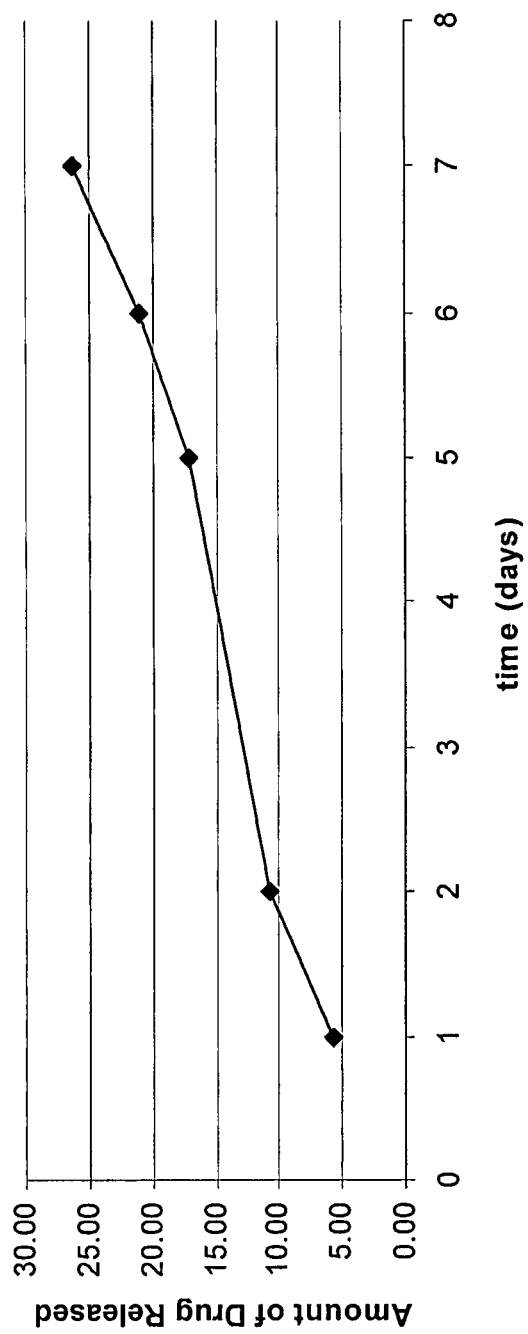
FIG. 9 is a chart illustrating the release of an anti-proliferative drug over time from the coated mesh device, in accordance with one embodiment of the present invention.
Figure 10:
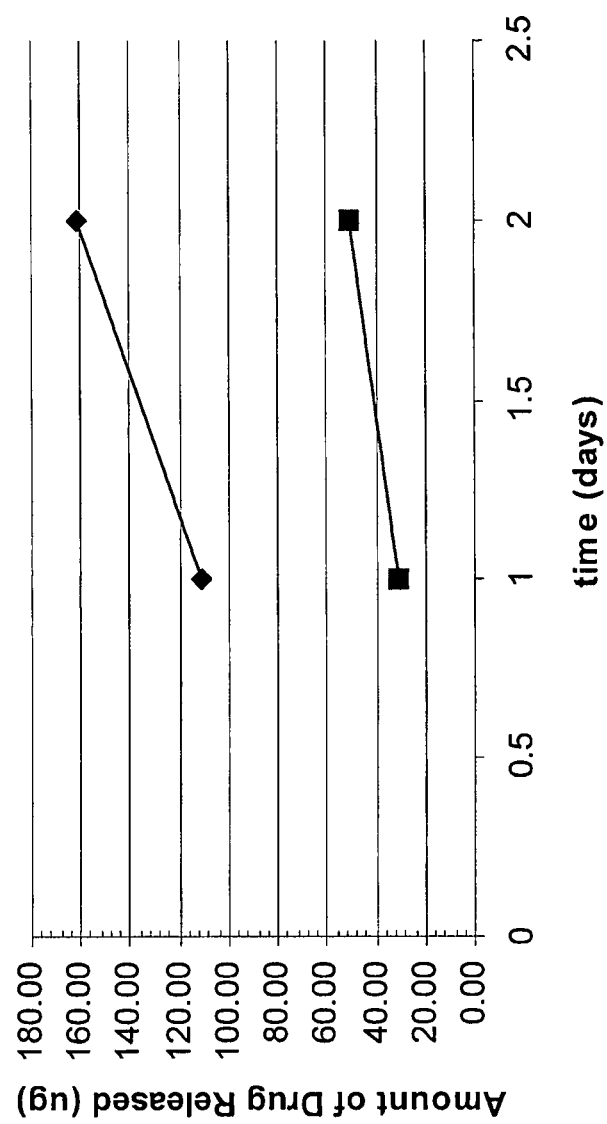
FIG. 10 is a graph illustrating the release of an anti-proliferative drug (♦) and a drug degradation product (■) over time from the coated mesh structure, in accordance with one embodiment of the present invention.
Figure 11:
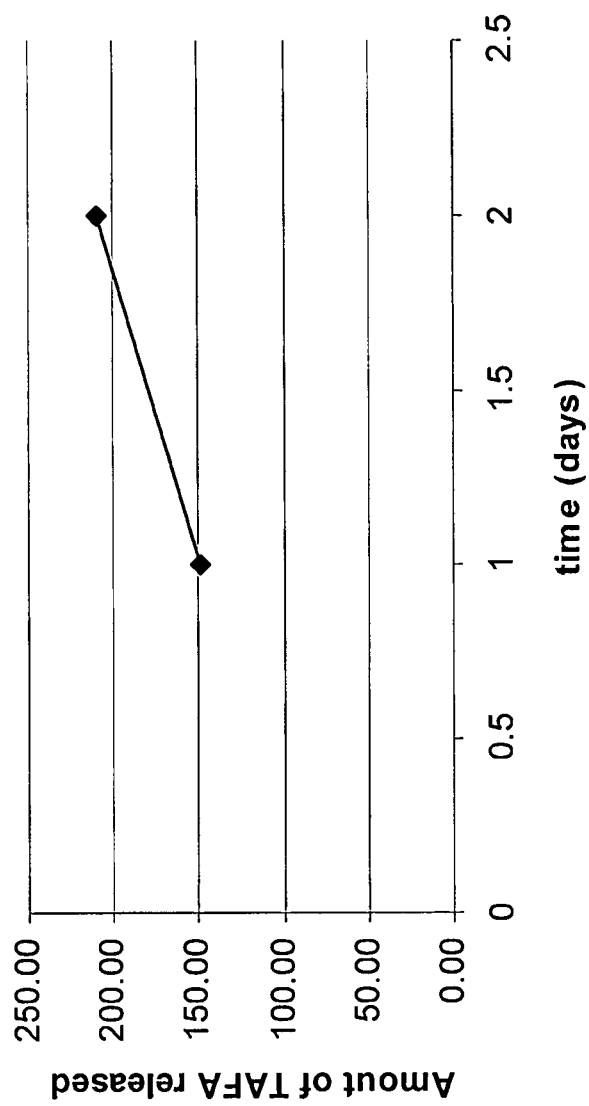
FIG. 11 is a chart illustrating the release of an anti-proliferative drug over time from the coated mesh structure, in accordance with one embodiment of the present invention.

FIG. 8 illustrates the release of an antiproliverative drug from a coated mesh structure coated with a coating derived from fish oil and vitamin E and loaded with an antiproliverative drug over a period of 8 days in 0.01 M PBS solution. FIG. 9 illustrates the release of an antiproliverative drug from a coated mesh structure coated with a coating derived from fish oil and vitamin E and loaded with an antiproliverative drug over a period of 8 days in 0.01 M PBS solution. FIG. 10 illustrates the release of an antiproliverative drug (♦) and a drug degradation product (■) from a coated mesh structure coated with a coating derived from fish oil and vitamin E and loaded with an antiproliverative drug over a period of 8 days in 0.01 M PBS solution. FIG. 11 illustrates the release of an antiproliverative drug standardized with the drug degradation product from a coated mesh structure coated with a coating derived from fish oil and vitamin E and loaded with an antiproliverative drug over a period of 8 days in 0.01 M PBS solution.

Figure 12:
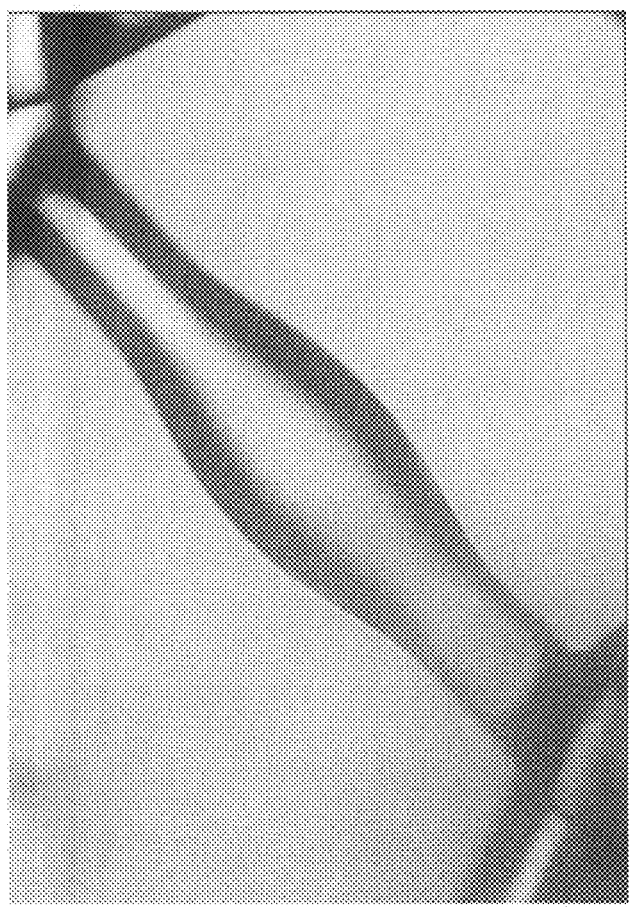
FIG. 12 is an is an optical microscopy image of an anti-proliferative drug-coated end of an untreated monofilament of the coated mesh structure, in accordance with one embodiment of the present invention.
Figure 13:
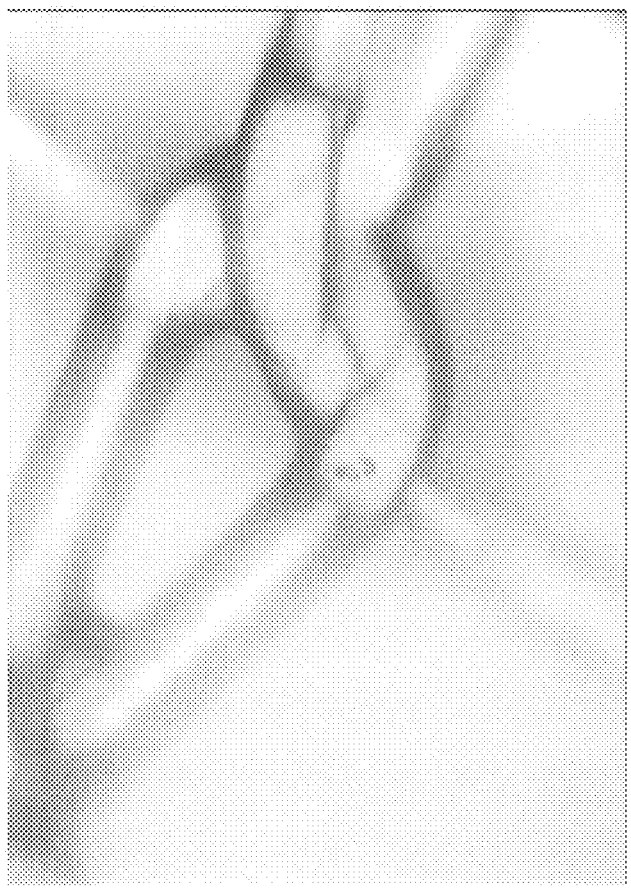
FIG. 13 is an optical microscopy image of an anti-proliferative drug-coated elevated loop of untreated monofilament of the coated mesh structure, in accordance with one embodiment of the present invention.

FIG. 12 is an optical microscopy image illustrating the coating distribution of an mesh monofiliment coated with a coating derived from fish oil and vitamin E and loaded with an antiproliverative drug. Similarly, FIG. 13 is an optical microscopy image illustrating the coating distribution of an mesh knit structure coated with a coating derived from fish oil and vitamin E and loaded with an antiproliverative drug.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the invention, and exclusive use of all modifications that come within the scope of the appended claims is reserved. It is intended that the present invention be limited only to the extent required by the appended claims and the applicable rules of law.

What is claimed is:

1. A coated surgical mesh comprising:
    a biocompatible mesh structure composed of a plurality of inter-coupled strands forming a plurality of interstices therebetween, wherein the mesh structure is not a stent; and
    a non-polymeric coating formed from one or more of fatty acids, glycerides or combinations thereof, wherein the one or more of fatty acids, glycerides or combinations thereof are cross-linked in a substantially random configuration, wherein the coating encapsulates the strands while maintaining the plurality of interstices uncoated.

2. The mesh of claim 1, wherein the coating further comprises vitamin E.

3. The mesh of claim 2, wherein the source of the one or more of fatty acids, glycerides or combinations thereof is fish oil, wherein the coating further comprises at least one therapeutic agent, and wherein a ratio of the fish oil to the vitamin E is variable prior to coating to increase the solubility of the therapeutic agent.

4. The mesh of claim 3, wherein the ratio of the fish oil to the vitamin E is at least about 80:20 by weight.

5. The mesh of claim 1, wherein the coating further comprises at least one therapeutic agent.

6. The mesh of claim 5, wherein the therapeutic agent is selected from the group consisting of antioxidants, anti-inflammatory agents, anti-coagulant agents, drugs to alter lipid metabolism, anti-proliferatives, anti-neoplastics, tissue growth stimulants, functional protein/factor delivery agents, anti-infective agents, imaging agents, anesthetic agents, chemotherapeutic agents, tissue absorption enhancers, anti-adhesion agents, germicides, analgesics, prodrugs and antiseptics.

7. The mesh of claim 5, wherein the coating is formulated to release the therapeutic agent in a controlled manner after implantation of the mesh in a subject.

8. The mesh of claim 1, wherein the coating is in at least a partially cured state prior to application of the coating on the mesh.

9. The mesh of claim 1, wherein the coating is subjected to curing conditions subsequent to application of the coating on the mesh, such that the coating is resident on the mesh in at least a partially cured state.

10. A method of making a coated surgical mesh, the method comprising:
providing a biocompatible mesh structure composed of a plurality of inter-coupled strands forming a plurality of interstices therebetween, wherein the mesh structure is not a stent;
preparing a coating formed from one or more of fatty acids, glycerides or combinations thereof, wherein the one or more of fatty acids, glycerides or combinations thereof are cross-linked in a substantially random configuration; and
applying the coating to the biocompatible mesh structure, wherein the coating encapsulates the strands while maintaining the plurality of interstices uncoated.

11. The method of claim 10, wherein the coating further comprises vitamin E.

12. The method of claim 10, wherein the source of the one or more of fatty acids, glycerides or combinations thereof is fish oil, and wherein the coating is prepared by mixing about 80% by weight of the fish oil with about 20% by weight vitamin E.

13. The method of claim 12, wherein the method further comprises the step of dissolving one or more therapeutic agents in the coating prior to application of the coating to the biocompatible mesh structure.

14. The method of claim 10, wherein the method further comprises the step of coating the biocompatible mesh structure with one or more therapeutic agents dissolved in a solvent.

15. The method of claim 10, wherein the coating further comprises between about 0.1 and 50% by weight of a therapeutic agent.

16. The method of claim 10, wherein the coating further comprises between about 6% and 7% by weight of a therapeutic agent.

17. The method of claim 10, wherein the coating is dispersed on the biocompatible mesh structure in the amount of about 15 mg/in$^2$.

18. The method of claim 10, wherein the method further comprises the step of treating the biocompatible mesh structure prior to application of the coating.

19. The method of claim 18, wherein the step of treating the biocompatible mesh structure prior to coating improves the adhesive forces between the coating and the mesh, diminishes coating flow and pooling and provides a more continuous coating.

20. The method of claim 10, wherein said coating is in at least a partially cured state prior to application of the coating on the mesh.

21. The method of claim 20, wherein curing comprises applying a curing mechanism selected from the group of curing mechanisms comprising heat, UV light, chemical means and reactive gasses.

22. The method of claim 10, further comprising the step of partially curing the coating after application of the coating to the biocompatible mesh structure.

23. The method of claim 22, wherein the step of partially curing comprises applying a curing mechanism selected from the group of curing mechanisms comprising heat, UV light, chemical means and reactive gasses.

24. The method of claim 10, wherein the method further comprises the step of packaging and sterilizing the biocompatible mesh structure and the coating.

25. The method of claim 24, wherein the step of sterilizing is performed by vaporized hydrogen peroxide, ethylene oxide (ETO) gas, radiation using gamma or electron-beam radiation, steam and gas plasma.

* * * * *

UNITED STATES PATENT AND TRADEMARK OFFICE
CERTIFICATE OF CORRECTION

| | | |
|---|---|---|
| PATENT NO. | : 8,574,627 B2 | Page 1 of 1 |
| APPLICATION NO. | : 11/978840 | |
| DATED | : November 5, 2013 | |
| INVENTOR(S) | : Martakos et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1117 days.

Signed and Sealed this
Tenth Day of March, 2015

Michelle K. Lee
*Deputy Director of the United States Patent and Trademark Office*